US012673060B2

(12) United States Patent
Thomas et al.

(10) Patent No.: US 12,673,060 B2
(45) Date of Patent: Jul. 7, 2026

(54) COMPOSITION AND METHODS FOR TREATING RESPIRATORY DISEASES

(71) Applicant: St. Jude Children's Research Hospital, Memphis, TN (US)

(72) Inventors: Paul Thomas, Memphis, TN (US); David F. Boyd, Memphis, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 750 days.

(21) Appl. No.: 17/996,554

(22) PCT Filed: Apr. 19, 2021

(86) PCT No.: PCT/IB2021/053221
§ 371 (c)(1),
(2) Date: Oct. 19, 2022

(87) PCT Pub. No.: WO2021/214637
PCT Pub. Date: Oct. 28, 2021

(65) Prior Publication Data

US 2023/0201208 A1 Jun. 29, 2023

Related U.S. Application Data

(60) Provisional application No. 63/012,578, filed on Apr. 20, 2020.

(51) Int. Cl.

| | |
|---|---|
| ***A61K 31/53*** | (2006.01) |
| ***A61K 31/4166*** | (2006.01) |
| ***A61K 45/06*** | (2006.01) |
| ***A61P 11/00*** | (2006.01) |
| ***A61P 31/00*** | (2006.01) |
| ***A61P 31/16*** | (2006.01) |

(52) U.S. Cl.
CPC .......... *A61K 31/53* (2013.01); *A61K 31/4166* (2013.01); *A61K 45/06* (2013.01); *A61P 11/00* (2018.01); *A61P 31/00* (2018.01); *A61P 31/16* (2018.01)

(58) Field of Classification Search
CPC .... A61K 31/4166; A61K 31/53; A61K 45/06; A61P 11/00; A61P 31/00; A61P 31/16
See application file for complete search history.

(56) References Cited

FOREIGN PATENT DOCUMENTS

WO WO-2010085246 A1 * 7/2010 .......... C07D 417/12

OTHER PUBLICATIONS

Boyd et al. (The J of Immunology, 196, Issue 1, May 2016) (Year: 2016).*
Nitsch-Osuch et al. (Adv Exp Medicine, Biology, Neuroscience and Respiration, 2016, 20, 25-31) (Year: 2016).*
Boyd, D., et al., "Exuberant fibroblast activity compromises lung function via ADAMTS4," *Nature*, 2020, vol. 587(7834) pp. 466-471.

* cited by examiner

*Primary Examiner* — Umamaheswari Ramachandran
(74) *Attorney, Agent, or Firm* — Womble Bond Dickinson (US) LLP

(57) ABSTRACT

Provided herein are compositions containing a therapeutically effective amount of at least one ADAMTS4 inhibitor, such as a specific ADAMTS4 inhibitor, and a therapeutically effective amount of at least one antibiotic, and the use of such compositions in treating an infection in a subject in need thereof. Also disclosed herein are methods for treating an infection in a subject in need thereof, by administering to the subject a therapeutically effective amount of at least one ADAMTS4 inhibitor, such as a specific ADAMTS4 inhibitor, and a therapeutically effective amount of at least one antibiotic.

15 Claims, 16 Drawing Sheets

| Cohort Location | No. Patients | Influenza Types | Sample Types | % Severe | % Female | Mean Age (range) |
|---|---|---|---|---|---|---|
| Taiwan | 37 | H1N1 (21)<br>H3N2 (11)<br>Influenza B (5) | Sputum (73%)<br>BAL (27%) | 40.0 | 55.6 | 54.8 ± 24.0<br>(6 - 88) |
| Guangzhou | 30 | H7N9 (16)<br>H1N1 (14) | Sputum (35%)<br>BAL (25%)<br>ETA (40%) | 79.3 | 30.0 | 52.8 ± 14.8<br>(17 - 74) |

FIG. 4B

COMPOSITION AND METHODS FOR TREATING RESPIRATORY DISEASES

CROSS-REFERENCE TO RELATED APPLICATIONS

This application is a national stage filing under 35 U.S.C. 371 of PCT/IB2021/053221 filed Apr. 19, 2021, which was published by the International Bureau in English on Oct. 28, 2021, and which claims priority from U.S. Provisional Application No. 63/012,578, filed Apr. 20, 2020, each of which is hereby incorporated in its entirety by reference in this application.

STATEMENT OF GOVERNMENT SUPPORT

This invention was made with government support under grant number HSSN272201400006C awarded by the National Institutes of Health. The government has certain rights in the invention.

FIELD OF THE INVENTION

The invention relates to compositions and methods comprising an ADAMTS4 inhibitor and an antibiotic for treating infections in a subject.

BACKGROUND

Respiratory infections are a leading cause of morbidity and mortality globally. These infections, caused by a variety of pathogens, can result in acute lung injury (ALI) and acute respiratory distress syndrome (ARDS), characterized by severely compromised lung function (Forum of International Respiratory Societies & European Respiratory Society. *The global impact of respiratory disease* (2017); Bhattacharya & Matthay, *Ann Rev Physiol* 75:593-615 (2013)). Much of the lung damage induced by viral infection is a result of infiltrating immune cells, which migrate to the site of infection and kill infected and bystander cells (Duan & Thomas, *Front Immunol* 7: (2016)). Thus, there is unmet need for identifying mechanistic targets to alter the balance between pathogen clearance and immunopathology to improve outcomes following severe respiratory infections leading to ARDS4.

Influenza, more commonly known as the flu, is an acute viral infection that attacks mainly the upper respiratory tract, including the nose, throat and bronchi, and rarely also the lungs. Although the flu is considered to be an infection of the respiratory tract, individuals suffering from the flu usually become acutely ill with high fever, chills, headache, weakness, loss of appetite and aching joints. The typical length of time from when a person is exposed to influenza virus to when symptoms first occur ranges between one and five days, with an average of two days. Adults can be infectious (i.e., shedding virus) starting the day before the onset of symptoms begin until approximately 5 days after the onset of illness. Children can be infectious for longer periods of time. Systemic symptoms include abrupt onset of fever (e.g., usually 100-103 degrees F. in an adult and possibly higher in children), chills, headaches, myalgia and malaise.

Although people recover within one to two weeks without requiring any medical treatment, influenza poses a serious risk in the very young, the elderly, and people suffering from medical conditions such as lung diseases, diabetes, cancer, kidney or heart problems. In these people, influenza infection may lead to severe complications of underlying diseases, pneumonia and death. Also, influenza infections are known to increase the susceptibility of an infected person to particular bacterial infections caused by species of bacterial pathogens such as, the pneumococcus, staphylococcus, mycoplasma, non-group *H. influenza*, and *Moraxella catarrhalis*. Secondary bacterial infections, such as, but not limited to infections of the lower respiratory tract (e.g., pneumonia), middle ear infections (e.g., otitis media) and bacterial sinusitis are common complications of an infection with viral influenza.

Given that the flu and its associated complications (e.g., bacterial infections, viral pneumonia, and cardiac and other organ system abnormalities) represent the sixth leading cause of death in the world and the leading infectious cause of death, there is an unmet need for improved therapeutics and methods for the treatment of viral diseases and disorders, such as the flu and its related conditions.

SUMMARY OF THE INVENTION

Provided herein are compositions containing a therapeutically effective amount of at least one ADAMTS4 inhibitor, such as a specific ADAMTS4 inhibitor, and a therapeutically effective amount of at least one antibiotic, and the use of such compositions in treating an infection in a subject in need thereof. Also disclosed herein are methods for treating an infection in a subject in need thereof, by administering to the subject a therapeutically effective amount of at least one ADAMTS4 inhibitor, such as a specific ADAMTS4 inhibitor, and a therapeutically effective amount of at least one antibiotic.

Accordingly, in one aspect, the disclosure provides a pharmaceutical composition comprising a therapeutically effective amount of at least one ADAMTS4 inhibitor and a therapeutically effective amount of at least one antibiotic.

In some embodiments of the pharmaceutical composition, the ADAMTS4 inhibitor is a specific Adamts4 inhibitor.

In certain embodiments of the pharmaceutical composition, the ADAMTS4 inhibitor is a compound represented by formula (I)

(I)

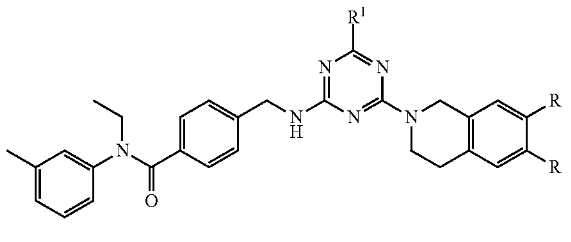

wherein R is OMe; and $R^1$ is

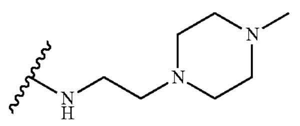 [SMILES: *NCCN1CCN(C)CC1]

or a pharmaceutically acceptable salt thereof.

In particular embodiments of the pharmaceutical composition, the ADAMTS4 inhibitor is 4-(((4-(6,7-dimethoxy-3,4-dihydroisoquinolin-2(1H)-yl)-6-(((4-methylpiperazin-1- yl)methyl)amino)-1,3,5-triazin-2-yl)amino)methyl)-N-ethyl-N-(m-tolyl)benzamide, or a pharmaceutically acceptable salt thereof.

In certain embodiments of the pharmaceutical composition, the ADAMTS4 inhibitor is a compound represented by formula (II)

(II)

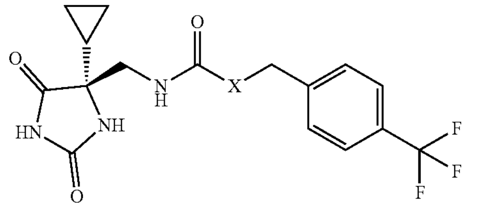

wherein X is

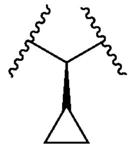

or a pharmaceutically acceptable salt thereof.

In particular embodiments of the pharmaceutical composition, the ADAMTS4 inhibitor is (S)-2-Cyclopropyl-N—(((R)-4-cyclopropyl-2,5-dioxoimidazolidin-4-yl)methyl)-3-(4-(trifluoromethyl)phenyl)-propanamide.

In some embodiments of the pharmaceutical composition, the antibiotic is a broad spectrum antibiotic.

In certain embodiments of the pharmaceutical composition, the antibiotic is selected from the group consisting of an aminoglycoside, an ampicillin, an amoxicillin/clavulanic acid, a carbapenem, a piperacillin/tazobactam, a quinolone, a tetracycline, a chloramphenicol, a ticarcillin, an azithromycin, and a trimethoprim/sulfamethoxazole. In particular embodiments of the pharmaceutical composition, the antibiotic is effective against *Streptococcus pneumoniae.*

In some embodiments, the pharmaceutical composition further comprises a pharmaceutically acceptable carrier.

In some embodiments, the pharmaceutical composition is in a unit dosage form.

In some embodiments, the pharmaceutical composition comprises about 5-10,000 mg of the ADAMTS4 inhibitor. In certain embodiments, the pharmaceutical composition comprises about 50-5,000 mg of the ADAMTS4 inhibitor. In certain embodiments, the pharmaceutical composition comprises about 100-1,000 mg of the ADAMTS4 inhibitor. In certain embodiments, the pharmaceutical composition comprises about 200-500 mg of the ADAMTS4 inhibitor.

In some embodiments, the pharmaceutical composition comprises at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the ADAMTS4 inhibitor.

In some embodiments, the pharmaceutical composition comprises about 5-10,000 mg of the antibiotic. In certain embodiments, the pharmaceutical composition comprises about 50-5,000 mg of the antibiotic. In certain embodiments, the pharmaceutical composition comprises about 100-1,000 mg of the antibiotic. In certain embodiments, the pharmaceutical composition comprises about 200-500 mg of the antibiotic.

In some embodiments, the pharmaceutical composition comprises at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the antibiotic.

In some embodiments, the ADAMTS4 inhibitor and the antibiotic are co-formulated. In alternative embodiments, the ADAMTS4 inhibitor and the antibiotic are formulated separately.

In some embodiments, the pharmaceutical composition further comprises one or more antiviral therapeutic. In some instances, the antiviral therapeutic is effective against influenza virus.

In certain embodiments, the antiviral therapeutic is a neuraminidase inhibitor. In particular embodiments, the neuraminidase inhibitor is selected from the group consisting of oseltamivir, laninamivir, peramivir, and zanamivir. In specific embodiments, the neuraminidase inhibitor is oseltamivir.

In certain embodiments, the antiviral therapeutic is baloxavir marboxil.

In another aspect, the present disclosure provides a use of a pharmaceutical composition described hereinabove in treating an infection in a subject in need thereof.

In another aspect, the present disclosure provides a pharmaceutical composition comprising a therapeutically effective amount of at least one ADAMTS4 inhibitor and a therapeutically effective amount of at least one antibiotic for use in treating an infection in a subject in need thereof.

In another aspect, the present disclosure provides a method for treating an infection in a subject in need thereof, the method comprising administering to the subject a therapeutically effective amount of at least one ADAMTS4 inhibitor and a therapeutically effective amount of at least one antibiotic.

In some embodiments of the method, treating an infection comprises reducing at least one symptom of the infection. In certain embodiments of the method, the at least one symptom is a symptom of a secondary bacterial infection developed following a viral infection. In particular embodiments of the method, the symptom of a secondary bacterial infection is one or more of fever, chills or rigors, pleuritic chest pain, cough productive of mucopurulent, rusty sputum, dyspnea, tachypnea or tachycardia, hypoxia, malaise, nausea, vomiting, and/or headache.

In some embodiments of the method, the ADAMTS4 inhibitor is a specific ADAMTS4 inhibitor.

In certain embodiments of the method, the ADAMTS4 inhibitor is a compound represented by formula (I)

(I)

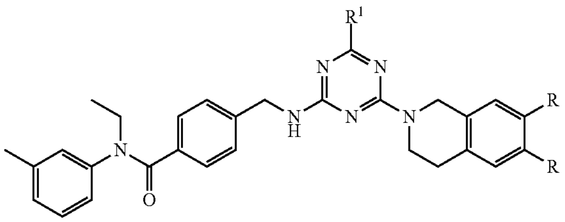

wherein R is OMe; and $R^1$ is

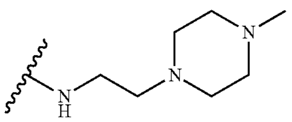

or a pharmaceutically acceptable salt thereof.

In particular embodiments of the method, the ADAMTS4 inhibitor is 4-(((4-(6,7-dimethoxy-3,4-dihydroisoquinolin-2(1H)-yl)-6-(((4-methylpiperazin-1-yl)methyl)amino)-1,3,5-triazin-2-yl)amino)methyl)-N-ethyl-N-(m-tolyl)benzamide, or a pharmaceutically acceptable salt thereof.

In certain embodiments of the method, the ADAMTS4 inhibitor is a compound represented by formula (II)

(II)

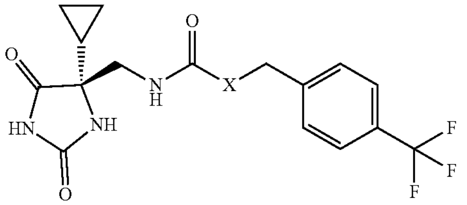

wherein X is

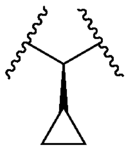

or a pharmaceutically acceptable salt thereof.

In particular embodiments of the method, the ADAMTS4 inhibitor is (S)-2-Cyclopropyl-N—(((R)-4-cyclopropyl-2,5-dioxoimidazolidin-4-yl)methyl)-3-(4-(trifluoromethyl)phenyl)-propanamide.

In some embodiments of the method, the antibiotic is a broad spectrum antibiotic.

In certain embodiments of the method, the antibiotic is selected from the group consisting of an aminoglycoside, an ampicillin, an amoxicillin/clavulanic acid, a carbapenem, a piperacillin/tazobactam, a quinolone, a tetracycline, a chloramphenicol, a ticarcillin, an azithromycin, and a trimethoprim/sulfamethoxazole.

In particular embodiments of the method, the antibiotic is effective against *Streptococcus pneumoniae*. In specific embodiments of the method, the antibiotic kills or prevents or reduces the growth of *Streptococcus pneumoniae* by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more.

In some embodiments, the method comprises administering about 5-10,000 mg of the ADAMTS4 inhibitor. In certain embodiments, the method comprises administering about 50-5,000 mg of the ADAMTS4 inhibitor. In certain embodiments, the method comprises administering about 100-1,000 mg of the ADAMTS4 inhibitor. In certain embodiments, the method comprises administering about 200-500 mg of the ADAMTS4 inhibitor.

In some embodiments, the method comprises administering at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the ADAMTS4 inhibitor.

In some embodiments, the method comprises administering about 5-10,000 mg of the antibiotic. In certain embodiments, the method comprises administering about 50-5,000 mg of the antibiotic. In certain embodiments, the method comprises administering about 100-1,000 mg of the antibiotic. In certain embodiments, the method comprises administering about 200-500 mg of the antibiotic.

In some embodiments, the method comprises administering at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the antibiotic.

In some embodiments, the method comprises administering the antibiotic prior to administering the ADAMTS4 inhibitor. In certain embodiments, the method comprises administering the antibiotic about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 8 h, 10 h, 12 h, 18 h, 24 h, 36 h, 48 h, 72 h, 96 h, 5 days, 6 days, 1 week, 2 weeks, 3 weeks, or 4 weeks prior to administering the ADAMTS4 inhibitor.

In some embodiments, the method comprises administering the antibiotic subsequent to administering the ADAMTS4 inhibitor. In certain embodiments, the method comprises administering the antibiotic about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 8 h, 10 h, 12 h, 18 h, 24 h, 36 h, 48 h, 72 h, 96 h, 5 days, 6 days, 1 week, 2 weeks, 3 weeks, or 4 weeks subsequent to administering the ADAMTS4 inhibitor.

In some embodiments, the method comprises administering the antibiotic and the ADAMTS4 inhibitor concomitantly.

In some embodiments, the method comprises administering one dose of the ADAMTS4 inhibitor and the antibiotic.

In alternative embodiments, the method comprises administering 2, 3, 4, 5, 6, 7, 8, 9, 10, 11, 12, 13, 14, 15, 16, 17, 18, 19, 20, or more doses of the ADAMTS4 inhibitor and the antibiotic. In some such embodiments, each dose is administered about 1 h, 2 h, 3 h, 4 h, 5 h, 6 h, 8 h, 10 h, 12 h, 18 h, 24 h, 36 h, 48 h, 72 h, 96 h, 5 days, 6 days, 1 week, 2 weeks, 3 weeks, or 4 weeks after the immediately preceding dose.

In some embodiments, the method is repeated daily, once every 2 days, once every 3 days, once every 4 days, once every 6 days, once every week, once every 2 weeks, once every 3 weeks, once every 4 weeks, once every month, once every 2 months, once every 3 months, once every 4 months, once every 5 months, once every 6 months, once every 7 months, once every 8 months, once every 9 months, once every 10 months, once every 11 months, or once every year.

In some embodiments, the method comprises oral administration of the ADAMTS4 inhibitor and the antibiotic to the subject.

In alternative embodiments, the method comprises parenteral administration of the ADAMTS4 inhibitor and the antibiotic to the subject. In some such embodiments, the method comprises intravenous, intra-arterial or subcutaneous administration of the ADAMTS4 inhibitor and the antibiotic to the subject.

In some embodiments, the ADAMTS4 inhibitor and the antibiotic are co-formulated as a pharmaceutical composition. In alternative embodiments, the ADAMTS4 inhibitor and the antibiotic are formulated as separate pharmaceutical compositions. In certain embodiments, the pharmaceutical composition further comprises a pharmaceutically acceptable carrier.

In some embodiments, the method further comprises administering one or more antiviral therapeutic. In certain embodiments, the antiviral therapeutic is effective against influenza virus. In particular embodiments, the antiviral therapeutic inhibits or reduces an immune reaction, and/or delays the onset of an immune reaction associated with or caused by influenza virus by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more.

In certain embodiments, the antiviral therapeutic is a neuraminidase inhibitor. In particular embodiments, the neuraminidase inhibitor is selected from the group consisting of oseltamivir, laninamivir, peramivir, and zanamivir. In specific embodiments, the neuraminidase inhibitor is oseltamivir.

In certain embodiments, the antiviral therapeutic is baloxavir marboxil.

In some embodiments, the method reduces inflammation, immune cell infiltration, and/or tissue damage associated with the infection. In certain embodiments, the method reduces mRNA and/or protein expression of one or more inflammatory cytokines or chemokines. In particular embodiments, the method reduces mRNA and/or protein expression of TNFA and MCP-1.

In some embodiments of the method, the infection is a respiratory infection. In certain embodiments of the method, the infection is a viral infection. In some such embodiments, the infection is influenza.

In some embodiments of the method, the subject is at a risk of developing a secondary bacterial infection. In additional or alternative embodiments of the method, the subject shows one or more symptoms of and/or is diagnosed with a secondary bacterial infection.

In some such embodiments, the secondary bacterial infection is caused by *Streptococcus pneumoniae, Haemophilus influenzae, Staphylococcus aureus*, and/or *Streptococcus pyogenes.*

In some embodiments of the method, the subject is a mammal. In some such embodiments of the method, the subject is a human.

BRIEF DESCRIPTION OF THE DRAWING

FIG. 1A provides heatmap representing the average log 2 fold-change values relative to mock-infected mice (n=3-5 mice per time point) at the indicated days after infection with 2500 $EID_{50}$ IAV PR8. Ct values were measured by qRT-PCR in RNA isolated from whole lung homogenates. ΔCt values were determined (normalized to Actb) for each gene and used to calculate fold-change based on ΔΔCt calculation. Genes on the y-axis are grouped by hierarchical clustering, and the top upregulated genes are presented. FIG. 1B provides t-stochastic neighbor embedding (t-SNE) clustering of all murine lung cells based on single-cell gene expression profiling. Data from all time points (0, 1, 3, and 6 days post-infection) and mice (n=4-5 mice per time point) were aggregated; ~40,800 individual cells are represented in the figure. FIG. 1C is a dot plot of key genes related to cytokine/chemokine induction and ECM-production and modification in human lung mesenchymal cells. Color-coding indicates average relative expression, while the size of the dot indicates percent of cells expressing the gene in the indicated cluster.

FIG. 2 is a heatmap representing log 2 fold-change values (relative to ACTB and normalized to untreated cells) in normal human bronchial fibroblasts (NHBFs) and normal human bronchial epithelial cells (NHBEs) stimulated with the indicated cytokines. Green shading highlights stimulation with IL-1 cytokines and TNFA while blue shading indicates stimulation with IAVs. Data represent the mean of two independent biological replicates performed with duplicate stimulations.

FIG. 3A depicts survival curves following lethal IAV PR8 challenge (6000 $EID_{50}$), ADAMTS-$4^{+/+}$ (WT), n=33; ADAMTS-$4^{-/-}$ (KO), n=23. Curves were compared using Log-rank Test. Data are pooled from five independent experiments. FIG. 3B provides histological scores of H&E staining and IAV NP IHC from uninfected, ADAMTS-4-/-, and ADAMTS-4+/+ lungs sampled at 9 dpi following challenge with sublethal dose of PR8 (2500 $EID_{50}$) (ADAMTS-$4^{+/+}$, n=10; ADAMTS-$4^{-/-}$, n=9). FIG. 3C depicts frequency of IFNg+CD8+ T cells from whole lungs collected at 9 dpi following stimulation with PMA/ionomycin. Representative flow plots of IFNg staining are presented at the right. FIG. 3D provides frequency and total number of tetramer+CD8+ T cells from whole lungs collected at 9 dpi. Representative flow plots of peptide:MHC tetramer staining are presented below. FIG. 3E depicts measurement of airway resistance and dynamic lung compliance in uninfected, ADAMTS-4-/-, and ADAMTS-$4^{+/+}$ mice following challenge with a sublethal dose of PR8 (2500 $EID_{50}$). Mice were challenged with methacholine at the indicated concentrations (Uninfected, n=11; ADAMTS-4+/+, n=8; ADAMTS-4-/-, n=9). Unless otherwise indicated, data are pooled from two independent experiments. Error bars indicate standard error of the mean (SEM). For statistical analysis, groups were compared using a two-sided Mann-Whitney U test.

FIGS. 4A-4F provides data showing association of lower respiratory tract ADAMTS-4 levels with severe seasonal and avian influenza infections. FIG. 4A is a schematic of influenza infection cohorts in Taiwan and Guangzhou with respect to disease severity. FIG. 4B provides demographic and sample information for Taiwan and Guangzhou cohorts. Moderate cases were defined as those requiring a hospital of less than 20 days, while severe cases were defined as those requiring a hospital stay of greater than 20 days or having death as an outcome. FIG. 4C provides correlation matrix plot of informative analytes from the first available time point for each patient in Taiwan and Guangzhou cohorts following log 10 transformation of protein concentrations. For each pairwise comparison, color-coding indicates the Spearman correlation coefficient while the size of the box indicates significance level. Analytes are arranged by hierarchical clustering. FIG. 4D provides scatter plots with regression lines of analytes significantly correlated with ADAMTS-4. Samples are color-coded according to severity, moderate (blue) and severe (red). FIG. 4E depicts compartmentalization of MMP-3 and ADAMTS-4 in samples from upper (nasal wash) and lower (sputum, BALF, ETA) respiratory tracts. FIG. 4F provides comparison of log 10 transformed ADAMTS-4 protein concentrations in samples from moderate and severe cases. Analysis was conducted on non-zero values using linear mixed models in order to control for longitudinal sampling.

DETAILED DESCRIPTION OF THE INVENTION

1.1 References and Definitions

Figure 1A:
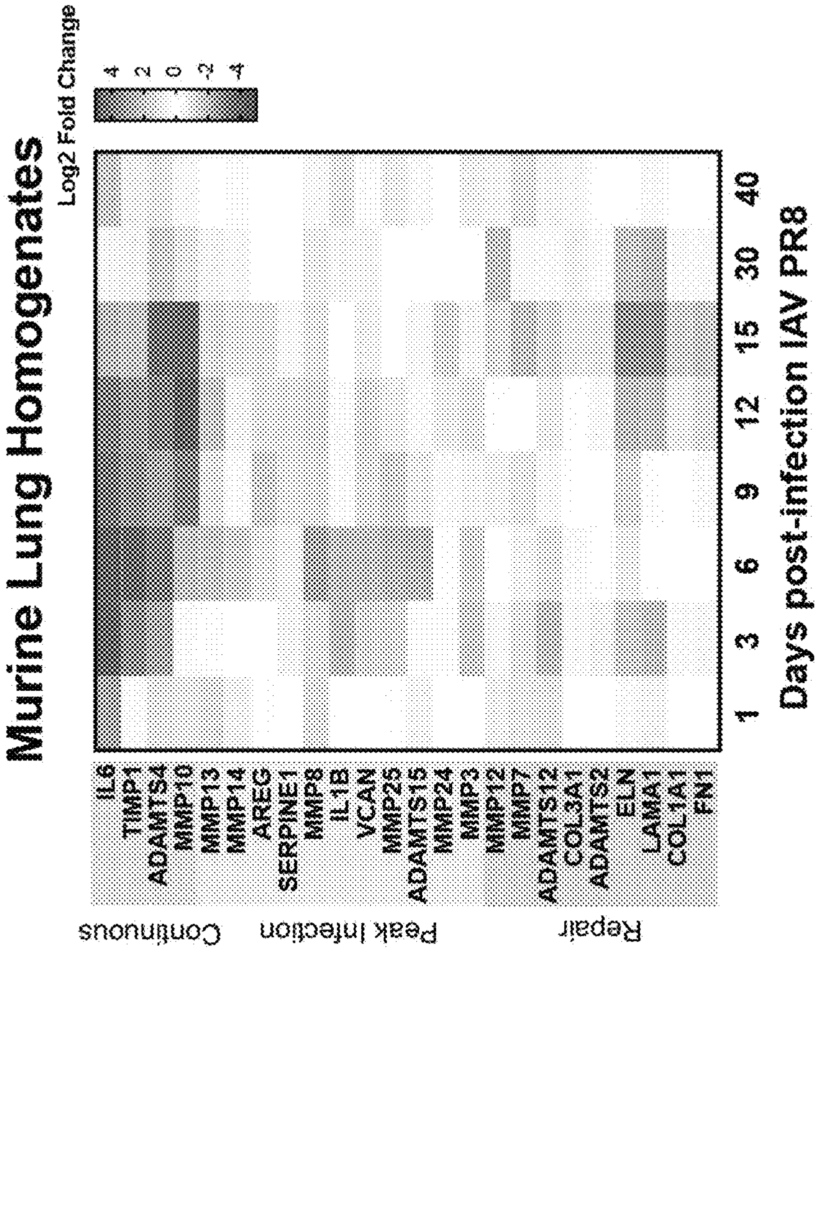
FIGS. 1A-1C provides data showing distinct antiviral and tissue-damage responses in fibroblasts during severe influenza virus infection.

The patent and scientific literature referred to herein establishes knowledge that is available to those of skill in the art. The issued US patents, allowed applications, published foreign applications, and references, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used in the specification and the appended claims, the singular forms "a," "an" and "the" include plural referents unless the context clearly dictates otherwise. Thus, for example, reference to "an ADAMTS4 inhibitor," "an antibiotic" or "an antiviral therapeutic" can include mixtures of two or more such ADAMTS4 inhibitor, antibiotic, or antiviral therapeutic, and the like.

As used herein, unless specifically indicated otherwise, the word "or" is used in the inclusive sense of "and/or" and not the exclusive sense of "either/or."

The term "about" or "approximately" usually means within 5%, or more preferably within 1%, of a given value or range.

The terms "comprises", "comprising", "includes", "including", "having" and their conjugates mean "including but not limited to".

Various embodiments of this disclosure may be presented in a range format. It should be noted that whenever a value or range of values of a parameter are recited, it is intended that values and ranges intermediate to the recited values are also part of this disclosure. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1-10 should be considered to have specifically disclosed subranges such as from 1 to 3, from 1 to 4, from 1 to 5, from 1 to 6, from 1 to 7, from 1 to 8, from 1 to 9, from 2 to 4, from 2 to 6, from 2 to 8, from 2 to 10, from 3 to 6, etc., as well as individual numbers within that range, for example, 1, 2, 3, 4, 5, 6, 7, 8, 9 and 10. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein, the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject who shows symptoms and/or complications of one or more infections, is diagnosed with one or more infections, or is under the treatment of a clinician, e.g., physician for one or more infections. The term "patient" includes human and veterinary subjects. In various aspects, the one or more infections are one or more respiratory infections, such as viral infections (e.g., influenza infection).

As used herein, the term "treatment" refers to the medical management of a subject, such as a patient with the intent to cure, ameliorate, stabilize, or prevent a disease, pathological condition, or disorder, such as one or more infections described hereinabove. This term includes active treatment (treatment directed to improve the disease, pathological condition, or disorder), causal treatment (treatment directed to the cause of the associated disease, pathological condition, or disorder), palliative treatment (treatment designed for the relief of symptoms or complications associated with the disease, pathological condition, or disorder), preventative treatment (treatment directed to delaying, minimizing or partially or completely inhibiting the development or onset of the associated disease, pathological condition, or disorder); and supportive treatment (treatment employed to supplement another therapy). Treatment also includes curing, suppressing, reducing, alleviating, and/or ameliorating one or more symptoms and/or complications associated with a disease, pathological condition, or disorder, such as one or more infections described hereinabove. For example, treatment can include reducing at least one symptom of a viral and/or a bacterial infection described herein. In some embodiments, treatment includes reducing at least one symptom of a bacterial infection, such as a secondary bacterial infection that develops following a viral infection. In some embodiments, treatment includes reducing at least one symptom of a bacterial infection, such as a secondary bacterial infection caused by administration of anti-viral therapeutics. In certain embodiments, the secondary bacterial infection is caused by *Streptococcus pneumoniae*. For example, treatment can include reducing at least one symptom of a bacterial infection caused by *Streptococcus pneumoniae*, such as reducing one or more of fever, chills or rigors, pleuritic chest pain, cough productive of mucopurulent, rusty sputum, dyspnea, tachypnea or tachycardia, hypoxia, malaise or weakness, nausea, vomiting, and/or headache caused by *Streptococcus pneumoniae*. In particular, treatment can include reducing at least one symptom of a viral and/or a bacterial infection described herein by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. For example, treatment can include reducing at least one symptom of a bacterial infection caused by *Streptococcus pneumoniae*, by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. A suitable control may be a similar symptom in a control subject, such as, a test subject before receiving the treatment method described herein, or a different subject or group of subjects with like symptoms as the test subject, who did not receive the treatment described herein. For example, treatment can include reducing at least one symptom of a bacterial infection caused by *Streptococcus pneumoniae*, by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a similar symptom in a control subject.

Treatment also includes prevention and/or delay of the onset of symptoms and/or complications associated with a disease, pathological condition, or disorder, such as one or more infections described hereinabove. Treatment also includes diminishment of the extent of the disease, pathological condition, or disorder, such as one or more infections described hereinabove; preventing spread of the disease, pathological condition, or disorder, such as one or more infections described hereinabove; delay or slowing the progress of the disease, pathological condition, or disorder, such as one or more infections described hereinabove; amelioration or palliation of the disease, pathological condition, or disorder, such as one or more infections described hereinabove; and remission (whether partial or total), whether detectable or undetectable. "Ameliorating" or "palliating" a disease, pathological condition, or disorder, such as one or more infections described hereinabove, means that the extent and/or undesirable clinical manifestations of the disease, condition, or disorder are lessened and/or time course of the progression is slowed or lengthened, as compared to the extent or time course in the absence of treatment. Treatment does not require the complete amelioration of a symptom, complication, or disease and encompasses embodiments in which one reduces symptoms and/or underlying risk factors. "Treatment" can also mean prolonging survival as compared to expected survival if not receiving treatment. Those in need of treatment include those already with the condition or disorder, as well as those prone to have the condition or disorder or those in which the condition or disorder is to be prevented. The term "prevent" does not require the 100% elimination of the possibility of an event. Rather, it denotes that the likelihood of the occurrence of the event has been reduced in the presence of the compound or method. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, such as arresting its development; or (iii) relieving the disease, such as causing regression of the disease. In certain embodiments, a disease, pathological condition, or disorder includes one or more infections described herein. Additionally, or alternatively, a disease, pathological condition, or disorder may include symptoms and/or complications associated with one or more infections described herein. For example, a disease, pathological condition, or disorder may include immune reaction (e.g., inflammation, immune cell infiltration, and/or tissue damage) associated with one or more infections described herein.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the ADAMTS4 inhibitor and antibiotic, compositions, or methods disclosed herein. In some aspects of the disclosed methods, the subject has been diagnosed with a need for treatment of an infection, such as a respiratory infection (e.g., a viral infection, such as influenza) prior to the administering step. As used herein, a subject in need of a treatment may refer to selection of a subject based upon need for treatment of a disease, pathological condition, or disorder, such as one or more infections described herein. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intra-aural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically, such as administered to treat an existing disease or condition, such as one or more infections described herein. In further various aspects, a preparation can be administered prophylactically, such as administered for prevention of a disease or condition, such as one or more infections described herein.

As used herein, the term "effective amount" or "amount effective" or "therapeutically effective amount" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a therapeutic at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a prophylactically effective amount, such as an amount effective for prevention of a disease or condition.

As used herein with reference to an ADAMTS4 inhibitor, an antibiotic, and/or a composition (e.g., a pharmaceutical composition), the term "unit dosage form" refers to the amount of the ADAMTS4 inhibitor, the antibiotic, and/or the composition that is suitable for administration to a subject in a single dose. In some embodiments, a unit dosage form of an ADAMTS4 inhibitor, an antibiotic, and/or a composition (e.g., a pharmaceutical composition) described herein may encompass a therapeutically effective amount of the ADAMTS4 inhibitor, the antibiotic, and/or the composition.

The term "pharmaceutically acceptable" describes a material that is not biologically or otherwise undesirable, such as without causing an unacceptable level of undesirable biological effects or interacting in a deleterious manner.

Unless otherwise expressly stated, it is in no way intended that any method set forth herein be construed as requiring that its steps be performed in a specific order.

Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used herein with respect to a parameter, the term "reduce" or "reducing" or "decrease" or "decreasing" or "alleviate" or "alleviating" refers to a detectable (e.g., at least about 5%, 10%, 15%, 20%, 25%, 30%, 35%, 40%, 45%, 50%, 55%, 60%, 65%, 70%, 75%, 80%, 85%, 90%, 95%, 97%, 99%, or more) negative change in the parameter from a comparison control, e.g., an established normal or reference level of the parameter, or an established standard control. For example, as used herein, reducing or decreasing or alleviating symptoms and/or complications associated with an infection refers to detectable (e.g., at least about 5%, 10%, 15%, 20%, 25%, 30%, 35%, 40%, 45%, 50%, 55%, 60%, 65%, 70%, 75%, 80%, 85%, 90%, 95%, 97%, 99%, or more) negative change in symptoms and/or complications associated with the infection in a test subject (e.g., a subject who was subject to the methods of treatment described herein) compared to symptoms and/or complications associated with the infection in a control subject (e.g., the same subject before receiving the treatment method described herein; or a different subject, or group of subjects with like symptoms as the test subject, who did not receive the treatment described herein).

As used herein, a "control" or "control subject" refers to a subject who has not received the compositions and methods of the present disclosure. As used herein, a "test subject" refers to a subject who has received the compositions and methods of the present disclosure. As used herein with reference to a parameter, a "suitable control" may refer to the parameter in a control subject (e.g., a test subject before receiving the treatment method described herein; or a different subject, or group of subjects with like symptoms as the test subject, who did not receive the treatment described herein). For example, as used herein with reference to symptoms and/or complications associated with an infection, a "suitable control" may refer to symptoms and/or complications associated with the infection in a control subject (e.g., a test subject before receiving the treatment method described herein; or a different subject, or group of subjects with like symptoms as the test subject, who did not receive the treatment described herein).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. Certain features described in the context of various embodiments are not to be considered essential features of those embodiments, unless the embodiment is inoperative without those elements.

2.1 Compositions of the Invention

The present disclosure is directed to methods and compositions that can enhance the balance between pathogen clearance and immunopathology to improve treatment outcomes following severe respiratory infections leading to acute respiratory distress syndrome (ARDS).

Severe respiratory infections, including those caused by influenza viruses, can result in ARDS. Current treatment strategies are merely supportive, involving mechanical ventilation and control of fluid, and to date, there are no effective pharmacological therapeutics that can improve outcomes for patients with ARDS. Although the host inflammatory response is required to limit the spread of and eventually clear the pathogen, immunopathology is also known to be a major contributor to tissue damage. Respiratory viral infection can induce the emergence of multiple fibroblast populations, such as ECM-synthesizing, damage-responsive, and interferon-responsive fibroblasts. Exuberant activity of damage-responsive lung fibroblasts can drive lethal immunopathology during severe influenza virus infection. By producing matrix remodeling enzymes, in particular the matrix protease A disintegrin and metalloproteinase with thrombospondin motifs (ADAMTS) 4, and inflammatory cytokines, damage-responsive fibroblasts can modify the lung microenvironment to promote robust immune cell infiltration at the expense of lung function. In two retrospective human cohorts, the levels of ADAMTS-4 in the lower respiratory tract were associated with the severity of seasonal H1N1 and avian H7N9 influenza virus infections. Accordingly, a therapeutic agent that targets the matrix protease activity of damage-responsive lung fibroblasts could provide a promising approach to preserving lung function and improving clinical outcomes following severe respiratory infections. In some embodiments, methods and compositions described herein provide at least one Adamts4 inhibitor, such as a specific ADAMTS4 inhibitor for reducing immunopathology and lung injury caused by respiratory infections.

Also, respiratory infections, including those caused by influenza viruses, have now been found to increase the susceptibility of an infected person to particular bacterial infections caused by species of bacterial pathogens such as, the pneumococcus, staphylococcus, mycoplasma, non-group *H. influenza*, and *Moraxella catarrhalis*. Secondary bacterial infections, such as, but not limited to infections of the lower respiratory tract (e.g., pneumonia), middle ear infections (e.g., otitis media) and bacterial sinusitis are common complications of an infection with viral infections, such as influenza. Accordingly, to effectively improve the outcome of respiratory infections, it is critical to reduce such secondary bacterial infections. In some embodiments, methods and compositions described herein provide a combination of at least one ADAMTS4 inhibitor, such as a specific ADAMTS4 inhibitor, and at least one antibiotic.

2.2 ADAMTS4 Inhibitor

A disintegrin and metalloproteinase with thrombospondin motifs 4 (ADAMTS4) is an enzyme that in humans is encoded by the ADAMTS4 gene. This gene encodes a member of the ADAMTS (a disintegrin and metalloproteinase with thrombospondin motifs) protein family. Members of the family share several distinct protein modules, including a propeptide region, a metalloproteinase domain, a disintegrin-like domain, and a thrombospondin type 1 (TS) motif Individual members of this family differ in the number of C-terminal TS motifs, and some have unique C-terminal domains. ADAMTS4 is the shortest known ADAMTS, lacking the C-terminal domain and is the only non-glycosylated ADAMTS. It also only has one thrombospondin type 1 motif (TSR), whereas all the other ADAMTS have two or more TSRs. The TSR is important for binding of the enzyme to the extracellular matrix (ECM) and hence its substrate specificity. Adjacent to the C-terminal TSR is a disintegrin-like domain, a cysteine-rich region that stacks against the active-site of the enzyme when in its final folded tertiary structure (Kelwick et al., *Genome Biol* 16:113 (2015); Mosyak et al., *Protein Sci* 17: 16-21 (2008)). ADAMTS4 is capable of cleaving all the large chondroitin sulfate hyaluronan-binding proteoglycans (CSPGs), including aggrecan, brevican, neurocan and versican. Like ADAMTS5, it can be effectively inhibited by tissue inhibitor of metalloproteinase-3 (TIMP3) and this inhibition can be enhanced in the presence of aggrecan. In addition to TIMP3, it can also be inhibited by calcium pentosan polysulfate (Troeberg et al., *Matrix Biol* 28: 463-9 (2009); Wayne et al., J Biol Chem 282:20991-8 (2007); Takizawa et al., *FEBS Lett* 582:2945-9(2008)).

The present disclosure provides ADAMTS4 inhibitors for use in the methods and compositions described herein. In some embodiments, a therapeutically effective amount of an ADAMTS4 inhibitor can reduce the expression, activity and/or function of ADAMTS4. For example, a therapeutically effective amount of an ADAMTS4 inhibitor when administered to a subject (e.g., a mammalian subject, such as a human) by the methods described herein can reduce the expression, activity and/or function of ADAMTS4 in the subject. Expression of ADAMTS4 can be determined by measuring the mRNA expression and/or the protein expression of ADAMTS4. The mRNA and/or protein expression of ADAMTS4 can be measured by quantitative and semi-quantitative methods known in the art, including but not limited to RT-PCR, real-time quantitative RT-PCR (RT-qPCR or qPCR), western blotting, and ELISA. In certain embodiments, a therapeutically effective amount of an ADAMTS4 inhibitor when administered to a subject by the methods described herein can reduce the mRNA expression and/or protein expression of ADAMTS4 in the subject, as determined relative to a suitable control. A suitable control can be the mRNA expression and/or protein expression of ADAMTS4 in the same subject prior to administration of the ADAMTS4 inhibitor. Alternatively, a suitable control can be mRNA expression and/or protein expression of ADAMTS4 in a different subject, or group of subjects who are not administered the ADAMTS4 inhibitor. Activity and/or function of ADAMTS4 can be measured by methods known in the art, including, but not limited to: by measuring the aggrecanase activities of ADAMTS4, for example, by ELISA; by measuring the aggrecanase activities of ADAMTS4 with a recombinant aggrecan fragment and two monoclonal antibodies, as described, for example, in Will et al. (*J Biomol Tech* 16: 459-472 (2005)); by measuring the ability of ADAMTS4 to cleave the fluorogenic peptide substrate, Abz-TEGEARGSVI-Dap(Dnp)-KK—NH2; by using a fluorescence resonance energy transfer (FRET) substrate assay, as described, for example, in Roberts et al. (*Osteoarthritis Cartilage* 23: 1622-1626 (2015)); and/or by using an ADAMTS-4 detective fluorescent turn-on AuNP probe (ADAMTS-4-D-Au probe), as described, for example, in Peng et al. (*ACS Appl Mater Interfaces* 5: 6089-6096 (2013)). Activity and/or function of ADAMTS4 can also be measured by measuring the mRNA and/or protein expression of one or more enzymatic targets of ADAMTS-4, including, but not limited to, lung proteoglycan versican (VCAN). In certain embodiments, a therapeutically effective amount of an ADAMTS4 inhibitor when administered to a subject by the methods described herein can reduce the activity and/or function of ADAMTS4 in the subject, as determined relative to a suitable control. A suitable control can be the activity and/or function of ADAMTS4 in the same subject prior to administration of the ADAMTS4 inhibitor. Alternatively, a suitable control can be activity and/or function of ADAMTS4 in a different subject, or group of subjects who are not administered the ADAMTS4 inhibitor.

In some embodiments, a therapeutically effective amount of ADAMTS4 inhibitors described herein can reduce the expression, activity and/or function of ADAMTS4 by about 1-10%, 10-20%, 20-30%, 30-40%, 40-50%, 50-60%, 60-70%, 70-80%, 80-90%, 90-100%, or more (e.g., by about 5%, 10%, 15%, 20%, 25%, 30%, 35%, 40%, 45%, 50%, 55%, 60%, 65%, 70%, 75%, 80%, 85%, 90%, 95%, 97%, 99%, or more). For example, a therapeutically effective amount of an ADAMTS4 inhibitor when administered to a subject (e.g., a mammalian subject, such as a human) by the methods described herein can reduce the expression, activity and/or function of ADAMTS4 in the subject by about 1-10%, 10-20%, 20-30%, 30-40%, 40-50%, 50-60%, 60-70%, 70-80%, 80-90%, 90-100%, or more (e.g., by about 5%, 10%, 15%, 20%, 25%, 30%, 35%, 40%, 45%, 50%, 55%, 60%, 65%, 70%, 75%, 80%, 85%, 90%, 95%, 97%, 99%, or more), as determined relative to a suitable control. Additionally, or alternatively, a therapeutically effective amount of ADAMTS4 inhibitors described herein can reduce the expression, activity and/or function of ADAMTS4 by at least 10%, 15%, 20%, 25%, 30%, 35%, 40%, 45%, 50%, 55%, 60%, 65%, 70%, 75%, 80%, 85%, 90%, 95%, 97%, 99%, or more. For example, a therapeutically effective amount of an ADAMTS4 inhibitor when administered to a subject (e.g., a mammalian subject, such as a human) by the methods described herein can reduce the expression, activity and/or function of ADAMTS4 in the subject by at least 10%, 15%, 20%, 25%, 30%, 35%, 40%, 45%, 50%, 55%, 60%, 65%, 70%, 75%, 80%, 85%, 90%, 95%, 97%, 99%, or more, as determined relative to a suitable control. A suitable control can be activity and/or function of ADAMTS4 in the same subject prior to administration of the ADAMTS4 inhibitor. Alternatively, a suitable control can be activity and/or function of ADAMTS4 in a different subject, or group of subjects who are not administered the ADAMTS4 inhibitor.

In some embodiments, the ADAMTS4 inhibitors described herein are specific ADAMTS4 inhibitors, such as inhibitors that specifically reduce the activity and/or function of ADAMTS4, and do not affect the activity and/or function of other members of the ADAMTS family. For example, a specific ADAMTS4 inhibitor for use in the compositions and methods of the present disclosure may specifically reduce the activity and/or function of ADAMTS4, without affecting the activity and/or function of ADAMTS5. In certain embodiments, provided herein are one or more ADAMTS4 inhibitors, as described, for example, by Ding et al. (*ACS Med Chem Lett* 6:888-893 (2015)), the contents of which are incorporated herein by reference in its entirety. In some instances, an ADAMTS4 inhibitor for use in the methods and compositions described herein may be a compound that is represented by formula (I):

(I)

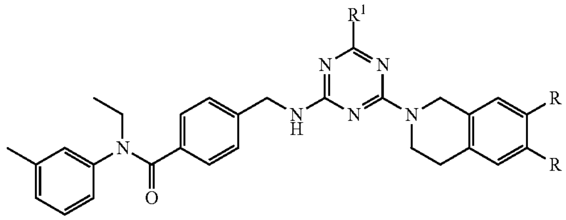

wherein R is OMe, and $R^1$ is

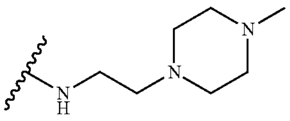

or a pharmaceutically acceptable salt thereof.

In certain embodiments, an ADAMTS4 inhibitor, such as a specific ADAMTS4 inhibitor for use in the methods and compositions described herein may be 4-(((4-(6,7-dimethoxy-3,4-dihydroisoquinolin-2(1H)-yl)-6-(((4-methylpiperazin-1-yl)methyl)amino)-1,3,5-triazin-2-yl)amino) methyl)-N-ethyl-N-(m-tolyl)benzamide, or a pharmaceutically acceptable salt thereof.

In certain embodiments, provided herein are one or more ADAMTS4 inhibitors, as described, for example, by Durham et al. (*J Med Chem* 60:5933-5939 (2017)), the contents of which are incorporated herein by reference in its entirety. In some instances, an ADAMTS4 inhibitor for use in the methods and compositions described herein may be a compound that is represented by formula (II):

(II)

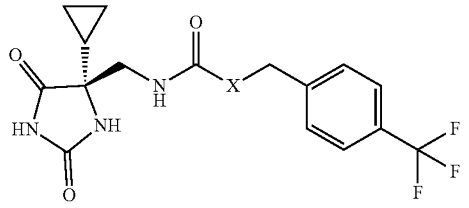

wherein X is or a pharmaceutically acceptable salt thereof.

In certain embodiments, an ADAMTS4 inhibitor, such as a specific ADAMTS4 inhibitor for use in the methods and compositions described herein may be (S)-2-Cyclopropyl-N—(((R)-4-cyclopropyl-2,5-dioxoimidazolidin-4-yl) methyl)-3-(4-(trifluoromethyl)phenyl)-propanamide, or a pharmaceutically acceptable salt thereof.

Pharmaceutically acceptable salts of an ADAMTS4 inhibitor, such as a specific ADAMTS4 inhibitor, may be conventional acid-addition salts or base-addition salts that retain the biological effectiveness and properties of the ADAMTS4 inhibitor and are formed from suitable non-toxic organic or inorganic acids or organic or inorganic bases. Exemplary acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Exemplary base-addition salts include those derived from ammonium, potassium, sodium and, quaternary ammonium hydroxides, such as for example, tetramethylammonium hydroxide. Chemical modification of a pharmaceutical compound (e.g., an ADAMTS4 inhibitor, such as a specific ADAMTS4 inhibitor) into a salt is a known technique to obtain improved physical and chemical stability, hygroscopicity, flowability and solubility of compounds. See, e.g., Ansel et. al, Pharmaceutical Dosage Forms and Drug Delivery Systems (6th Ed. 1995) at pp. 196 and 1456-1457.

In certain embodiments, the present disclosure also encompasses derivatives of ADAMTS4 inhibitors, such as specific ADAMTS4 inhibitors described herein. A derivative of an ADAMTS4 inhibitor may refer to a compound having a structure derived from the structure of a parent compound (e.g., an ADAMTS4 inhibitor, such as a specific ADAMTS4 inhibitor described herein) and whose structure is sufficiently similar to those disclosed herein. Based upon that similarity, a derivative of an ADAMTS4 inhibitor would be expected by one skilled in the art to exhibit the same or similar activities and utilities as the claimed compounds, or to induce, as a precursor, the same or similar activities and utilities as the ADAMTS4 inhibitor described herein. Exemplary derivatives include salts, esters, amides, salts of esters or amides, and N-oxides of an ADAMTS4 inhibitor described herein.

The ADAMTS4 inhibitor compounds described herein can be present as a solvate. In some cases, the solvent used to prepare the solvate is an aqueous solution, and the solvate is then often referred to as a hydrate. The ADAMTS4 inhibitor compounds can be present as a hydrate, which can be obtained, for example, by crystallization from a solvent or from aqueous solution. In this connection, one, two, three or any arbitrary number of solvate or water molecules can combine with the ADAMTS4 inhibitor compounds according to the disclosure to form solvates and hydrates.

Unless stated to the contrary, the present disclosure includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see, e.g., Almarasson et al., (2004) *The Royal Society of Chemistry,* 1889-1896. Examples of co-crystals include p-toluenesulfonic acid and benzenesulfonic acid.

It is known that chemical substances form solids which are present in different states of order which are termed polymorphic forms or modifications. The different modifications of a polymorphic substance can differ greatly in their physical properties. The ADAMTS4 inhibitor compounds according to the disclosure can be present in different polymorphic forms, with it being possible for particular modifications to be metastable. Unless stated to the contrary, the disclosure includes all such possible polymorphic forms.

2.3. Antibiotic

In some embodiments, the present disclosure provides at least one ADAMTS4 inhibitor, such as at least one specific ADAMTS4 inhibitor, and at least one antibiotic for use in the compositions and methods described herein. For example, the present disclosure may provide a composition containing a therapeutically effective amount of at least one ADAMTS4 inhibitor, and a therapeutically effective amount of at least one antibiotic. Additionally, the present disclosure may provide the use of a composition containing a therapeutically effective amount of at least one ADAMTS4 inhibitor, and a therapeutically effective amount of at least one antibiotic in treating an infection, such as a respiratory infection. Additionally, the present disclosure may provide methods of treating an infection, such as a respiratory infection in a subject (e.g., a human subject) by administering to the subject a therapeutically effective amount of at least one ADAMTS4 inhibitor, and a therapeutically effective amount of at least one antibiotic.

As used herein, the term "antibiotic" or "antibiotic activity" or "antibiotic that is effective against" can refer to any biological or chemical compound that kills, or prevents or reduces the growth and/or division of a microorganism. An antibiotic can have bacteriostatic or bactericidal activity. As used herein, microorganisms can be any bacteria, yeast, fungus, virus or other undesirable cell. In specific embodiments, the antibiotic kills or prevents or reduces the growth of a *Streptococcus* bacterium. For example, the antibiotic can kill or prevent or reduce the growth of a *Streptococcus* bacterium by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more. In some embodiments, the antibiotic has activity against *Streptococcus pneumoniae*. For example, the antibiotic can kill or prevent or reduce the growth of *Streptococcus pneumoniae* by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more.

In some embodiments, an antibiotic for use in the methods and compositions described herein may be an antibiotic belonging to the penicillin class or the beta-lactam class of antibiotics. For example, an antibiotic for use in the methods and compositions described herein may be an aminopenicillin, an antipseudomonal penicillin, a beta-lactamase inhibitor, a natural penicillin, and/or a penicillinase resistant penicillin. In certain embodiments, an antibiotic for use in the methods and compositions described herein may be an aminopenicillin, such as amoxicillin (e.g., Amoxil®, Moxatag®, etc.) or ampicillin (e.g., Principen®). Additionally, or alternatively, an antibiotic for use in the methods and compositions described herein may be an antipseudomonal penicillin, such as piperacillin (e.g., Pipracil®). Additionally, or alternatively, an antibiotic for use in the methods and compositions described herein may be a beta-lactamase inhibitor, such as amoxicillin/clavulanate (e.g., Augmentin®, Amoclan®, etc.), ampicillin/sulbactam (e.g., Unasyn®), or piperacillin/tazobactam (e.g., Zosyn®). Additionally, or alternatively, an antibiotic for use in the methods and compositions described herein may be a natural penicillin, such as penicillin g benzathine (e.g., Bicillin L-A®), or penicillin v (e.g., Penicillin VK®). Additionally, or alternatively, an antibiotic for use in the methods and compositions described herein may be a penicillinase resistant penicillin, such as dicloxacillin (e.g., Dycill®), nafcillin (e.g., Unipen®), or oxacillin (e.g., Bactocill®).

In some embodiments, an antibiotic for use in the methods and compositions described herein may be an antibiotic belonging to the tetracycline class. For example, an antibiotic for use in the methods and compositions described herein may be one or more of demeclocycline (e.g., Declomycin®), doxycycline (e.g., Adoxa®, Doryx®, Doxy 100®, Oracea®, Vibramycin®, etc.), eravacycline (e.g., Xerava®), minocycline (e.g., Dynacin®, Minocin®, Solodyn®, etc.), omadacycline (e.g., Nuzyra®), and/or tetracycline (e.g., Panmycin®, Sumycin®, etc.).

In some embodiments, an antibiotic for use in the methods and compositions described herein may be an antibiotic belonging to the cephalosporin class. For example, an antibiotic for use in the methods and compositions described herein may be one or more of cefaclor (e.g., Ceclor®), cefdinir (e.g., Omnicef®), cefotaxime (e.g., Claforan®), ceftazidime (e.g., Avycaz®, Fortaz®, Tazicef®, etc.), ceftriaxone (e.g., Rocephin®), and/or cefuroxime (e.g., Zinacef®).

In some embodiments, an antibiotic for use in the methods and compositions described herein may be an antibiotic belonging to the quinolones or the fluoroquinolone class. For example, an antibiotic for use in the methods and compositions described herein may be one or more of lomefloxacin (e.g., Maxaquin®), gatifloxacin (e.g., Tequin®), norfloxacin (e.g., Noroxin®), moxifloxacin (e.g., Avelox®, Avelox I.V.®, etc.), ofloxacin (e.g., Floxin®), delafloxacin (e.g., Baxdela®), ciprofloxacin (Cipro®, Cipro I.V.®, Cipro XR®, Proquin XR®, etc.), levofloxacin (e.g., Levaquin®), gemifloxacin (e.g., Factive®), nalidixic acid (e.g., NegGram®), cinoxacin (e.g., Cinobac®), trovafloxacin (e.g., Trovan®), and/or sparfloxacin (e.g., Zagam®).

In some embodiments, an antibiotic for use in the methods and compositions described herein may be an antibiotic belonging to the lincomycin class. For example, an antibiotic for use in the methods and compositions described herein may be one or more of clindamycin (e.g., Cleocin®, Cleocin T®, Evoclin®, etc.), and/or lincomycin (e.g., Lincocin®).

In some embodiments, an antibiotic for use in the methods and compositions described herein may be an antibiotic belonging to the macrolide class. For example, an antibiotic for use in the methods and compositions described herein may be one or more of azithromycin (e.g., Zithromax), clarithromycin (e.g., Biaxin®), erythromycin (e.g., E.E.S.®, Ery-Tab®, Eryc®, etc.).

In some embodiments, an antibiotic for use in the methods and compositions described herein may be an antibiotic belonging to the Sulfonamide class. For example, an antibiotic for use in the methods and compositions described herein may be one or more of sulfasalazine (e.g., Azulfidine®), and/or trimethoprim/sulfamethoxazole (TMP/SMX) or co-trimoxazole (e.g., Bactrim®, Bactrim DS®, Septra®, etc.).

In some embodiments, an antibiotic for use in the methods and compositions described herein may be an antibiotic belonging to the glycopeptide antibiotic class. For example, an antibiotic for use in the methods and compositions described herein may be one or more of dalbavancin (e.g., Dalvance®), oritavancin (e.g., Orbactiv®), telavancin (e.g., Vibativ®), and/or vancomycin (e.g., Firvanq®, Vancocin®).

In some embodiments, an antibiotic for use in the methods and compositions described herein may be an antibiotic belonging to the aminoglycoside class. For example, an antibiotic for use in the methods and compositions described herein may be one or more of gentamicin (e.g., Garamycin®, Genoptic®, etc.), tobramycin (e.g., TOBI®, Tobradex®, Tobrex®, etc.), and/or amikacin (e.g., Amikin®).

In some embodiments, an antibiotic for use in the methods and compositions described herein may be an antibiotic belonging to the carbapenem class. For example, an antibiotic for use in the methods and compositions described herein may be one or more of imipenem and cilastatin (e.g., Primaxin®), meropenem (e.g., Merrem®), doripenem (e.g., Doribax®), and/or ertapenem (e.g., Invanz®).

In certain embodiments, an antibiotic for use in the methods and compositions described herein may be a broad spectrum antibiotic. In specific embodiments, a broad spectrum antibiotic for use in the methods and compositions described herein may be an aminoglycoside, such as one or more of gentamicin (e.g., Garamycin®, Genoptic®, etc.), tobramycin (e.g., TOBI®, Tobradex®, Tobrex®, etc.), and/or amikacin (e.g., Amikin®). Additionally, or alternatively, a broad spectrum antibiotic for use in the methods and compositions described herein may be an ampicillin (e.g., Principen®). Additionally, or alternatively, a broad spectrum antibiotic for use in the methods and compositions described herein may be an amoxicillin/clavulanic acid (e.g., Augmentin®, Amoclan®, etc.). Additionally, or alternatively, a broad spectrum antibiotic for use in the methods and compositions described herein may be a carbapenem, such as one or more of imipenem and cilastatin (e.g., Primaxin®), meropenem (e.g., Merrem®), doripenem (e.g., Doribax®), and/or ertapenem (e.g., Invanz®). Additionally, or alternatively, a broad spectrum antibiotic for use in the methods and compositions described herein may be a piperacillin/tazobactam (e.g., Zosyn®). Additionally, or alternatively, a broad spectrum antibiotic for use in the methods and compositions described herein may be a quinolone, such as one or more of lomefloxacin (e.g., Maxaquin®), gatifloxacin (e.g., Tequin®), norfloxacin (e.g., Noroxin®), moxifloxacin (e.g., Avelox®, Avelox I.V.®, etc.), ofloxacin (e.g., Floxin®), delafloxacin (e.g., Baxdela®), ciprofloxacin (Cipro®, Cipro I.V.®, Cipro XR®, Proquin XR®, etc.), levofloxacin (e.g., Levaquin®), gemifloxacin (e.g., Factive®), nalidixic acid (e.g., NegGram®), cinoxacin (e.g., Cinobac®), trovafloxacin (e.g., Trovan®), and/or sparfloxacin (e.g., Zagam®). Additionally, or alternatively, a broad spectrum antibiotic for use in the methods and compositions described herein may be a tetracycline, such as one or more of demeclocycline (e.g., Declomycin®), doxycycline (e.g., Adoxa®, Doryx®, Doxy 100®, Oracea®, Vibramycin®, etc.), eravacycline (e.g., Xerava®), minocycline (e.g., Dynacin®, Minocin®, Solodyn®, etc.), omadacycline (e.g., Nuzyra®), and/or tetracycline (e.g., Panmycin®, Sumycin®, etc.). Additionally, or alternatively, a broad spectrum antibiotic for use in the methods and compositions described herein may be a chloramphenicol (e.g., Pentamycetin, Chloromycetin, etc.). Additionally, or alternatively, a broad spectrum antibiotic for use in the methods and compositions described herein may be a ticarcillin. Additionally, or alternatively, a broad spectrum antibiotic for use in the methods and compositions described herein may be a macrolide, such as one or more of azithromycin (e.g., Zithromax), clarithromycin (e.g., Biaxin®), and/or erythromycin (e.g., E.E.S.®, Ery-Tab®, Eryc®, etc.). Additionally, or alternatively, a broad spectrum antibiotic for use in the methods and compositions described herein may be a trimethoprim/sulfamethoxazole (TMP/SMX) (e.g., Bactrim®, Bactrim DS®, Septra®, etc.).

In certain embodiments, an antibiotic for use in the methods and compositions described herein may be an antibiotic that is effective against *Streptococcus pneumoniae*. In particular, an antibiotic effective against *Streptococcus pneumoniae* is an antibiotic that kills *Streptococcus pneumoniae*. Additionally, or alternatively, an antibiotic effective against *Streptococcus pneumoniae* is an antibiotic that limits, inhibits, reduces, and/or delays the growth and/or division of *Streptococcus pneumoniae*. For example, an antibiotic effective against *Streptococcus pneumoniae* can be an antibiotic that limits, inhibits, reduces, and/or delays the growth and/or division of *Streptococcus pneumoniae* by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more.

In particular, an antibiotic effective against *Streptococcus pneumoniae* can limit, inhibit, reduce, and/or delay the growth and/or division of *Streptococcus pneumoniae* in a subject (e.g., a test subject) by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. A suitable control can be the same test subject prior to initiating the treatment with the antibiotic. Alternatively, a suitable control can be a different subject, or group of subjects with like symptoms as the test subject, who do not receive the treatment with the antibiotic. In some instances, growth and/or division of *Streptococcus pneumoniae* is measured by standard bacterial enumeration methods known in the art, including but not limited to: direct count of cells, such as direct count of cells using a counting chamber, or direct count of cells using fluorescent dyes; indirect count of cells, such as indirect count of cells using viable plate count, or indirect count of cells using the most probable number (MPN); direct measurement of microbial biomass; and/or indirect measurement of microbial biomass. Additionally, or alternatively, growth and/or division of *Streptococcus pneumoniae* can be measured by other methods known in the art, including but not limited to: real-time PCR, such as real-time PCR using primers and a fluorescent probe specific for pneumolysin gene, as described, for example, in Greiner et al. (*J Clin Microbiol* 39: 3129-3134 (2001)), and Park et al. (*FEMS Microbiol Lett* 310: 48-53 (2010)); and/or quantitative multiplex real-time PCR assay, as described, for example, in Fukushima et al. (*J Clin Microbiol* 46: 2384-2388 (2008)), and Ganaie et al. (*Pneumonia* 6: 57-66 (2015)).

2.4. Antiviral Therapeutic

In some embodiments, the present disclosure further provides one or more antiviral therapeutic for use in the compositions and methods described herein. For example, the present disclosure may provide a composition containing a therapeutically effective amount of at least one ADAMTS4 inhibitor (e.g., a specific ADAMTS4 inhibitor), a therapeutically effective amount of at least one antibiotic, and one or more antiviral therapeutics. Additionally, the present disclosure may provide the use of a composition containing a therapeutically effective amount of at least one ADAMTS4 inhibitor, a therapeutically effective amount of at least one antibiotic, and one or more antiviral therapeutics in treating an infection, such as a respiratory infection. Additionally, the present disclosure may provide methods of treating an infection, such as a respiratory infection in a subject (e.g., a human subject) by administering to the subject a therapeutically effective amount of at least one ADAMTS4 inhibitor, a therapeutically effective amount of at least one antibiotic, and one or more antiviral therapeutics.

As used herein, the term "antiviral therapeutic" or "antiviral therapeutic activity" or "antiviral therapeutic that is effective against" can refer to any biological or chemical compound that inhibits or reduces an immune reaction, and/or delays the onset of an immune reaction associated with or caused by a virus. In specific embodiments, the antiviral therapeutic inhibits or reduces an immune reaction, and/or delays the onset of an immune reaction associated with or caused by influenza virus. For example, the antiviral therapeutic can inhibit or reduce an immune reaction, and/or delay the onset of an immune reaction associated with or caused by influenza virus by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more.

In some embodiments, an antiviral therapeutic for use in the methods and compositions described herein may be an adamantane antiviral. For example, an antiviral therapeutic for use in the methods and compositions described herein may be one or more of amantadine (e.g., Symmetrel®), and/or rimantadine (e.g., Flumadine®).

In some embodiments, an antiviral therapeutic for use in the methods and compositions described herein may be an antiviral booster. For example, an antiviral therapeutic for use in the methods and compositions described herein may be one or more of ritonavir (e.g., Norvir®), and/or cobicistat (e.g., Tybost®).

In some embodiments, an antiviral therapeutic for use in the methods and compositions described herein may be an antiviral combination, such as an antiviral therapeutic that has more than one antiviral agent in one pill or dose. For example, an antiviral therapeutic for use in the methods and compositions described herein may be one or more of emtricitabine/tenofovir (e.g., AccessPak for HIV PEP Basic), emtricitabine/lopinavir/ritonavir/tenofovir (e.g., AccessPak for HIV PEP Expanded with Kaletra), emtricitabine/nelfinavir/tenofovir (e.g., AccessPak for HIV PEP Expanded with Viracept), efavirenz/emtricitabine/tenofovir (e.g., Atripla®), bictegravir/emtricitabine/tenofovir alafenamide (e.g., Biktarvy®), lamivudine/tenofovir (e.g., Cimduo®), lamivudine/zidovudine (e.g., Combivir®), emtricitabine/rilpivirine/tenofovir (e.g., Complera®), doravirine/lamivudine/tenofovir (e.g., Delstrigo®), emtricitabine/tenofovir alafenamide (e.g., Descovy®), dolutegravir/lamivudine (e.g., Dovato®), sofosbuvir/velpatasvir (e.g., Epclusa®), abacavir/lamivudine (e.g., Epzicom®), atazanavir/cobicistat (e.g., Evotaz®), cobicistat/elvitegravir/emtricitabine/tenofovir alafenamide (e.g., Genvoya®), ledipasvir/sofosbuvir (e.g., Harvoni®), dolutegravir/rilpivirine (e.g., Juluca®), glecaprevir/pibrentasvir (e.g., Mavyret®), emtricitabine/rilpivirine/tenofovir alafenamide (e.g., Odefsey®), cobicistat/darunavir (e.g., Prezcobix®), cobicistat/elvitegravir/emtricitabine/tenofovir (e.g., Stribild®), efavirenz/lamivudine/tenofovir (e.g., Symfi®), efavirenz/lamivudine/tenofovir (e.g., Symfi Lo®), cobicistat/darunavir/emtricitabine/tenofovir alafenamide (e.g., Symtuza®), ombitasvir/paritaprevir/ritonavir (e.g., Technivie®), lamivudine/tenofovir (e.g., Temixys®), abacavir/dolutegravir/lamivudine (e.g., Triumeq®), abacavir/lamivudine/zidovudine (e.g., Trizivir®), emtricitabine/tenofovir (e.g., Truvada®), dasabuvir/ombitasvir/paritaprevir/ritonavir (e.g., Viekira Pak®), dasabuvir/ombitasvir/paritaprevir/ritonavir (e.g., Viekira XR®), sofosbuvir/velpatasvir/voxilaprevir (e.g., Vosevi®), and/or elbasvir/grazoprevir (e.g., Zepatier®).

In some embodiments, an antiviral therapeutic for use in the methods and compositions described herein may be an antiviral interferon. For example, an antiviral therapeutic for use in the methods and compositions described herein may be one or more of peginterferon alfa-2a (e.g., Pegasys®), and/or peginterferon alfa-2b (e.g., PegIntron®, Sylatron®, etc.).

In some embodiments, an antiviral therapeutic for use in the methods and compositions described herein may be a chemokine receptor antagonist. For example, an antiviral therapeutic for use in the methods and compositions described herein may be maraviroc (e.g., Selzentry®).

In some embodiments, an antiviral therapeutic for use in the methods and compositions described herein may be an integrase strand transfer inhibitor. For example, an antiviral therapeutic for use in the methods and compositions described herein may be one or more of raltegravir (e.g., Isentress®), dolutegravir (e.g., Tivicay®), elvitegravir (e.g., Vitekta®).

In some embodiments, an antiviral therapeutic for use in the methods and compositions described herein may be a miscellaneous antiviral. For example, an antiviral therapeutic for use in the methods and compositions described herein may be one or more of fomivirsen (e.g., Vitravene®), sofosbuvir (e.g., Sovaldi®), baloxavir marboxil (e.g., Xofluza®), enfuvirtide (e.g., Fuzeon®), foscarnet (e.g., Foscavir®), letermovir (e.g., Prevymis®), and/or ibalizumab (e.g., Trogarzo®).

In some embodiments, an antiviral therapeutic for use in the methods and compositions described herein may be a neuraminidase inhibitor. For example, an antiviral therapeutic for use in the methods and compositions described herein may be one or more of zanamivir (e.g., Relenza®), oseltamivir (e.g., Tamiflu®), and/or peramivir (e.g., Rapivab®).

In some embodiments, an antiviral therapeutic for use in the methods and compositions described herein may be a non-nucleoside reverse transcriptase inhibitor (NNRTI). For example, an antiviral therapeutic for use in the methods and compositions described herein may be one or more of etravirine (e.g., Intelence®), efavirenz (e.g., Sustiva®), nevirapine (e.g., Viramune®), rilpivirine (e.g., Edurant®), doravirine (e.g., Pifeltro®), delavirdine (e.g., Rescriptor®), and/or nevirapine (e.g., Viramune XR®).

In some embodiments, an antiviral therapeutic for use in the methods and compositions described herein may be a non-structural protein 5A (NS5A) inhibitor. For example, an antiviral therapeutic for use in the methods and compositions described herein may be daclatasvir (e.g., Daklinza®).

In some embodiments, an antiviral therapeutic for use in the methods and compositions described herein may be a nucleoside reverse transcriptase inhibitor (NRTI). For example, an antiviral therapeutic for use in the methods and compositions described herein may be one or more of entecavir (e.g., Baraclude®), lamivudine (e.g., Epivir-HBV®, Epivir®, etc.), adefovir (e.g., Hepsera®), didanosine (e.g., Videx®), tenofovir alafenamide (e.g., Vemlidy®), abacavir (e.g., Ziagen®), tenofovir (e.g., Viread®), zidovudine (e.g., Retrovir®), stavudine (e.g., Zerit®), emtricitabine (e.g., Emtriva®), zalcitabine (e.g., Hivid®), telbivudine (e.g., Tyzeka®), and/or didanosine (e.g., Videx EC®).

In some embodiments, an antiviral therapeutic for use in the methods and compositions described herein may be a protease inhibitor. For example, an antiviral therapeutic for use in the methods and compositions described herein may be one or more of boceprevir (e.g., Victrelis®), simeprevir (e.g., Olysio®), fosamprenavir (e.g., Lexiva®), lopinavir/ritonavir (e.g., Kaletra®), darunavir (e.g., Prezista®), telaprevir (e.g., Incivek®), tipranavir (e.g., Aptivus®), ritonavir (e.g., Norvir®), atazanavir (e.g., Reyataz®), nelfinavir (e.g., Viracept®), amprenavir (e.g., Agenerase®), indinavir (e.g., Crixivan®), saquinavir (e.g., Fortovase®), and/or saquinavir (e.g., Invirase®).

In some embodiments, an antiviral therapeutic for use in the methods and compositions described herein may be a purine nucleoside. For example, an antiviral therapeutic for use in the methods and compositions described herein may be one or more of ribavirin (e.g., Ribasphere®), valacyclovir (e.g., Valtrex®), acyclovir (e.g., Zovirax®), acyclovir (e.g., Sitavig®), famciclovir (e.g., Famvir®), ribavirin (e.g., Copegus®, Moderiba®, Rebetol®, RibaPak®, RibaTab®, Virazole®, etc.), valganciclovir (e.g., Valcyte®), ganciclovir (e.g., Cytovene®), and/or cidofovir (e.g., Vistide®).

In certain embodiments, an antiviral therapeutic for use in the methods and compositions described herein is an antiviral therapeutic that is effective against influenza virus (e.g., influenza A virus and/or influenza B virus). In particular, an antiviral therapeutic effective against influenza virus is an antiviral therapeutic that inhibits or reduces an immune reaction, and/or delays the onset of an immune reaction associated with or caused by influenza virus. For example, an antiviral therapeutic effective against influenza virus can be an antiviral therapeutic that inhibits or reduces an immune reaction, and/or delays the onset of an immune reaction associated with or caused by influenza virus by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more. In particular, an antiviral therapeutic effective against influenza virus can inhibit or reduce an immune reaction, and/or delay the onset of an immune reaction associated with or caused by influenza virus in a subject (e.g., a test subject) by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. A suitable control can be the same test subject prior to initiating the treatment with the antiviral therapeutic. Alternatively, a suitable control can be a different subject, or group of subjects with like symptoms as the test subject, who do not receive the treatment with the antiviral therapeutic.

2.4. Therapeutic Compositions

The present disclosure also provides compositions containing at least one (e.g., at least one, two, three, four, five, six, seven, eight, nine, ten, or more) ADAMTS4 inhibitor and at least one (e.g., at least one, two, three, four, five, six, seven, eight, nine, ten, or more) antibiotic described hereinabove. For example, the present disclosure may provide a composition containing: (i) at least one, two, three, four, five, six, seven, eight, nine, ten, or more ADAMTS4 inhibitors described hereinabove; and (ii) at least one, two, three, four, five, six, seven, eight, nine, ten, or more antibiotics described hereinabove. In some embodiments, the ADAMTS4 inhibitor is a specific ADAMTS4 inhibitor, such as a specific ADAMTS4 inhibitor described hereinabove. In additional or alternative embodiments, the antibiotic is a broad spectrum antibiotic, such as a broad spectrum antibiotic described hereinabove. For example, the present disclosure may provide a composition containing: (i) at least one, two, three, four, five, six, seven, eight, nine, ten, or more specific ADAMTS4 inhibitors described hereinabove; and (ii) at least one, two, three, four, five, six, seven, eight, nine, ten, or more broad spectrum antibiotics described hereinabove.

In some embodiments, a composition described herein contains a therapeutically effective amount of at least one ADAMTS4 inhibitor, such as a therapeutically effective amount of at least one specific ADAMTS4 inhibitor. In particular, a therapeutically effective amount of an ADAMTS4 inhibitor may be at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the Adamts4 inhibitor. For example, a therapeutically effective amount of an ADAMTS4 inhibitor may be about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the Adamts4 inhibitor. In additional or alternative embodiments, a composition described herein contains a therapeutically effective amount of at least one antibiotic, such as a therapeutically effective amount of at least one broad spectrum antibiotic. In particular, a therapeutically effective amount of an antibiotic may be at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the antibiotic. For example, a therapeutically effective amount of an antibiotic may be about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of the antibiotic.

In some embodiments, a composition described herein is in unit dosage form. In certain embodiments, a composition described herein contains at least one ADAMTS4 inhibitor, such as at least one specific ADAMTS4 inhibitor, in a unit dosage form. In particular, a unit dosage form may contain at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of an Adamts4 inhibitor. For example, a unit dosage form may contain about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of an Adamts4 inhibitor. In additional or alternative embodiments, a composition described herein contains at least one antibiotic, such as at least one broad spectrum antibiotic, in a unit dosage form. In particular, a unit dosage form may contain at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one antibiotic. For example, a unit dosage form may contain about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one antibiotic.

In specific embodiments, a composition described herein may contain at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one Adamts4 inhibitor. For example, a composition described herein may contain about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one Adamts4 inhibitor. In additional or alternative embodiments, a composition described herein may contain at least 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one antibiotic. For example, a composition described herein may contain about 5-10,000 mg (e.g., about 10-10,000 mg, 25-7,500 mg, 50-5,000 mg, 75-2,500 mg, 100-1,000 mg, 150-750 mg, or 200-500 mg), or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more of at least one antibiotic.

In some embodiments, a composition of the present disclosure may contain at least one ADAMTS4 inhibitor(s) and at least one antibiotic(s), wherein the ADAMTS4 inhibitor(s) and the antibiotic(s) are co-formulated, such as co-formulated to form the composition. In other embodiments, a composition of the present disclosure may contain at least one ADAMTS4 inhibitor(s) and at least one antibiotic(s), wherein the ADAMTS4 inhibitor(s) and the antibiotic(s) are formulated separately, such as formulated separately and then mixed to form the composition.

In some embodiments, a composition of the present disclosure may further contain one or more antiviral therapeutics, such as one or more antiviral therapeutics described hereinabove. For example, a composition of the present disclosure may contain at least one ADAMTS4 inhibitor, at least one antibiotic, and one or more antiviral therapeutics described hereinabove. In certain embodiments, the antiviral therapeutic is a neuraminidase inhibitor, such as zanamivir (e.g., Relenza®), oseltamivir (e.g., Tamiflu®), and/or peramivir (e.g., Rapivab®). For example, a composition of the present disclosure may contain at least one ADAMTS4 inhibitor, at least one antibiotic, and one or more neuraminidase inhibitors described hereinabove. In certain embodiments, the antiviral therapeutic is baloxavir marboxil (e.g., Xofluza®). For example, a composition of the present disclosure may contain at least one ADAMTS4 inhibitor, at least one antibiotic, and baloxavir marboxil.

Pharmaceutical Composition

In some embodiments, a composition of the present disclosure is formulated as a pharmaceutical composition. In certain instances, a pharmaceutical composition contains a composition of the present disclosure and a pharmaceutically acceptable carrier. For example, a pharmaceutical composition described herein may contain at least one ADAMTS4 inhibitor, and at least one antibiotic in a pharmaceutically acceptable carrier. Alternatively, a pharmaceutical composition described herein may contain at least one ADAMTS4 inhibitor, at least one antibiotic, and one or more antiviral therapeutics in a pharmaceutically acceptable carrier.

In particular, a pharmaceutical composition described herein may contain a therapeutically effective amount of at least one ADAMTS4 inhibitor, and a therapeutically effective amount of at least one antibiotic in a pharmaceutically acceptable carrier. Alternatively, a pharmaceutical composition described herein may contain a therapeutically effective amount of at least one ADAMTS4 inhibitor, a therapeutically effective amount of at least one antibiotic, and one or more antiviral therapeutics in a pharmaceutically acceptable carrier.

A pharmaceutically acceptable carrier may refer to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. A composition of the present disclosure or one or more components therein (e.g., the at least one ADAMTS4 inhibitor and/or the at least one antibiotic) can be formulated with pharmaceutically acceptable carriers or diluents as well as any other known adjuvants and excipients in accordance with conventional techniques, such as those disclosed in Remington: The Science and Practice of Pharmacy, 19th Edition, Gennaro, Ed., Mack Publishing Co., Easton, Pa., 1995.

In some embodiments, a pharmaceutical composition disclosed herein may contain at least one ADAMTS4 inhibitor (including pharmaceutically acceptable salt(s) thereof) and at least one antibiotic as active ingredients, a pharmaceutically acceptable carrier, and, optionally, other therapeutic ingredients (e.g., one or more antiviral therapeutics described herein), and adjuvants. A pharmaceutical composition disclosed herein may include those suitable for oral administration, rectal administration, topical administration, inhalation, and parenteral (including subcutaneous, intramuscular, and intra-arterial, intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present disclosure suitable for parenteral administration can be prepared as solutions or suspensions of the active ingredients (e.g., at least one ADAMTS4 inhibitor (including pharmaceutically acceptable salt(s) thereof) and/or at least one antibiotic) in water. A suitable surfactant can be included, such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for injectable use may include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present disclosure can be in a form suitable for topical use, such as, for example, an aerosol, cream, ointment, lotion, dusting powder, mouth washes, gargles, and the like. Further, the compositions can be in a form suitable for use in transdermal devices. These formulations can be prepared, utilizing active ingredients (e.g., at least one ADAMTS4 inhibitor and/or at least one antibiotic) disclosed herein, or pharmaceutically acceptable salts thereof, via conventional processing methods. As an example, a cream or ointment is prepared by mixing hydrophilic material and water, together with about 5 wt % to about 10 wt % of the active ingredient, to produce a cream or ointment having a desired consistency.

Pharmaceutical compositions of this disclosure can be in a form suitable for rectal administration, wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations, such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or non-aqueous techniques. A tablet containing a composition of this disclosure can be prepared by compression or molding, optionally with one or more accessory ingredients or adjuvants. Compressed tablets can be prepared by compressing, in a suitable machine, the active ingredient in a free-flowing form, such as powder or granules, optionally mixed with a binder, lubricant, inert diluent, surface active or dispersing agent. Molded tablets can be made by molding in a suitable machine, a mixture of the powdered compound moistened with an inert liquid diluent.

In addition to the aforementioned carrier ingredients, the pharmaceutical formulations described hereinabove can include, as appropriate, one or more additional carrier ingredients, such as diluents, buffers, flavoring agents, binders, surface-active agents, thickeners, lubricants, preservatives (including anti-oxidants), and the like. Furthermore, other adjuvants can be included to render the formulation isotonic with the blood of the intended recipient. Compositions containing at least one ADAMTS4 inhibitor, at least one antibiotic, and optionally one or more antiviral therapeutic, can also be prepared in powder or liquid concentrate form.

In some embodiments, unit dosage form for the at least one ADAMTS4 inhibitor and unit dosage form for the at least one antibiotic are co-formulated. In such embodiments, unit dosage form for the at least one ADAMTS4 inhibitor and unit dosage form for the at least one antibiotic may be co-formulated for oral administration, inhalation, topical administration, and/or parenteral administration.

In other embodiments, unit dosage form for the at least one ADAMTS4 inhibitor and unit dosage form for the at least one antibiotic are formulated separately. In such embodiments, unit dosage form for the at least one ADAMTS4 inhibitor may be formulated for oral administration and unit dosage form for the at least one antibiotic may be formulated for parental administration. Alternatively, unit dosage form for the at least one ADAMTS4 inhibitor may be formulated for parental administration and unit dosage form for the at least one antibiotic may be formulated for oral administration. Alternatively, unit dosage form for the at least one ADAMTS4 inhibitor may be formulated for topical administration and unit dosage form for the at least one antibiotic may be formulated for parental administration. Alternatively, unit dosage form for the at least one ADAMTS4 inhibitor may be formulated for parental administration and unit dosage form for the at least one antibiotic may be formulated for topical administration. Alternatively, unit dosage form for the at least one ADAMTS4 inhibitor may be formulated for oral administration and unit dosage form for the at least one antibiotic may be formulated for inhalation. Alternatively, unit dosage form for the at least one ADAMTS4 inhibitor may be formulated for inhalation and unit dosage form for the at least one antibiotic may be formulated for oral administration. Alternatively, unit dosage form for the at least one ADAMTS4 inhibitor may be formulated for topical administration and unit dosage form for the at least one antibiotic may be formulated for inhalation. Alternatively, unit dosage form for the at least one ADAMTS4 inhibitor may be formulated for inhalation and unit dosage form for the at least one antibiotic may be formulated for topical administration.

In some embodiments, a pharmaceutical composition described herein may be formulated to release the at least one ADAMTS4 inhibitor and the at least one antibiotic immediately upon administration or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window at the site of release; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The pharmaceutical compositions may be sterilized by conventional sterilization techniques, or may be sterile filtered. The resulting aqueous solutions may be packaged for use as is or lyophilized. The lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting pharmaceutical compositions in solid form may, for example, be packaged in multiple single-dose units, each containing a fixed amount of at least one ADAMTS4 inhibitor and at least one antibiotic, and, optionally, one or more antiviral therapeutics, such as in a sealed package of tablets or capsules, or in a suitable dry powder inhaler (DPI) capable of administering one or more doses.

The pharmaceutical compositions can be prepared using standard methods known in the art by mixing the active ingredient (at least one ADAMTS4 inhibitor and at least one antibiotic, and, optionally, one or more antiviral therapeutics) having the desired degree of purity with, optionally, pharmaceutically acceptable carriers, excipients, or stabilizers (Remington's Pharmaceutical Sciences (20th edition), ed. A. Gennaro, 2000, Lippincott, Williams & Wilkins, Philadelphia, PA). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates, including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

2.5. Treatment

Further provided herein are methods for treating infections comprising administering an effective amount of at least on ADAMTS4 inhibitor and an effective amount of at least one antibiotic.

Regimen

In some instances, one or more infections in a subject can be treated according to a method of the present disclosure by administering to the subject one dose of at least one ADAMTS4 inhibitor and one dose of at least one antibiotic. Alternatively, one or more infections in a subject can be treated according to a method of the present disclosure by administering to the subject 2, 3, 4, 5, 6, 7, 8, 9, 10, 11, 12, 13, 14, 15, 16, 17, 18, 19, 20, or more doses of at least one ADAMTS4 inhibitor, and 2, 3, 4, 5, 6, 7, 8, 9, 10, 11, 12, 13, 14, 15, 16, 17, 18, 19, 20, or more doses of at least one antibiotic. In certain instances, each dose of at least one ADAMTS4 inhibitor and at least one antibiotic is administered about 1 h, 2 h, 3 h, 4 h, 5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks after the immediately preceding dose.

In some instances, the ADAMTS4 inhibitor and the antibiotic are formulated separately. In certain instances, the antibiotic is administered prior to administering the ADAMTS4 inhibitor. For example, one or more infections in a subject can be treated according to a method of the present disclosure by administering to the subject at least one ADAMTS4 inhibitor and at least one antibiotic, wherein the at least one antibiotic is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks prior to administering the at least one ADAMTS4 inhibitor. Alternatively, the antibiotic may be administered subsequent to administering the ADAMTS4 inhibitor. For example, one or more infections in a subject can be treated according to a method of the present disclosure by administering to the subject at least one ADAMTS4 inhibitor and at least one antibiotic, wherein the at least one antibiotic is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks subsequent to administering the at least one ADAMTS4 inhibitor. Alternatively, the antibiotic and the ADAMTS4 inhibitor may be administered concomitantly. For example, one or more infections in a subject can be treated according to a method of the present disclosure by administering to the subject at least one ADAMTS4 inhibitor and at least one antibiotic concomitantly.

In some instances, the ADAMTS4 inhibitor and the antibiotic are co-formulated. For example, at least one ADAMTS4 inhibitor and at least one antibiotic can be co-formulated to form a composition, such as a pharmaceutical composition described hereinabove. In some embodiments, the present disclosure provides methods for treating one or more infections in a subject in need thereof by administering to the subject a composition, such as a pharmaceutical composition described hereinabove. For example, the present disclosure may provide methods for treating one or more infections in a subject in need thereof by administering to the subject a composition, such as a pharmaceutical composition described hereinabove, wherein the composition contains a therapeutically effective amount of at least one ADAMTS4 inhibitor, and a therapeutically effective amount of at least one antibiotic. In some instances, one or more infections in a subject can be treated according to a method of the present disclosure by administering to the subject one dose of a pharmaceutical composition described hereinabove. Alternatively, one or more infections in a subject can be treated according to a method of the present disclosure by administering to the subject 2, 3, 4, 5, 6, 7, 8, 9, 10, 11, 12, 13, 14, 15, 16, 17, 18, 19, 20, or more doses of a pharmaceutical composition described hereinabove. In certain instances, each dose of a pharmaceutical composition described hereinabove is administered about 1 h, 2 h, 3 h, 4 h, 5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks after the immediately preceding dose.

In some instances, the method of treatment described hereinabove further includes administering one or more antiviral therapeutics.

In certain instances, a pharmaceutical composition described hereinabove includes one or more antiviral therapeutics. For example, the present disclosure may provide methods for treating one or more infections in a subject in need thereof by administering to the subject a composition, such as a pharmaceutical composition described hereinabove, wherein the composition contains a therapeutically effective amount of at least one ADAMTS4 inhibitor, a therapeutically effective amount of at least one antibiotic, and one or more antiviral therapeutics.

In certain instances, the one or more antiviral therapeutics is not included in a composition described hereinabove. In such instances, one or more antiviral therapeutics may be administered to a subject separately. For example, the present disclosure may provide methods for treating one or more infections in a subject in need thereof by administering to the subject one or more antiviral therapeutics, and a composition, such as a pharmaceutical composition described hereinabove, wherein the composition contains a therapeutically effective amount of at least one ADAMTS4 inhibitor, and a therapeutically effective amount of at least one antibiotic. In particular instances, the one or more antiviral therapeutics may be administered prior to administering the pharmaceutical composition. For example, one or more infections in a subject can be treated according to a method of the present disclosure by administering to the subject a pharmaceutical composition described hereinabove and one or more antiviral therapeutics, wherein the one or more antiviral therapeutics is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks prior to administering the pharmaceutical composition. Alternatively, the one or more antiviral therapeutics may be administered subsequent to administering the pharmaceutical composition. For example, one or more infections in a subject can be treated according to a method of the present disclosure by administering to the subject a pharmaceutical composition described hereinabove and one or more antiviral therapeutics, wherein the one or more antiviral therapeutics is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks subsequent to administering the pharmaceutical composition. Alternatively, the pharmaceutical composition and the one or more antiviral therapeutics may be administered concomitantly. For example, one or more infections in a subject can be treated according to a method of the present disclosure by administering to the subject a pharmaceutical composition described hereinabove and one or more antiviral therapeutics concomitantly.

In certain instances, the present disclosure may provide methods for treating one or more infections in a subject in need thereof by administering to the subject one or more antiviral therapeutics, a therapeutically effective amount of at least one ADAMTS4 inhibitor, and a therapeutically effective amount of at least one antibiotic. In particular instances, the one or more antiviral therapeutics may be administered prior to administering the ADAMTS4 inhibitor and/or the antibiotic. For example, one or more infections in a subject can be treated according to a method of the present disclosure by administering to the subject at least one ADAMTS4 inhibitor, at least one antibiotic, and one or more antiviral therapeutics, wherein the one or more antiviral therapeutics is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks prior to administering the ADAMTS4 inhibitor and/or the antibiotic. Alternatively, the one or more antiviral therapeutics may be administered subsequent to administering the ADAMTS4 inhibitor and/or the antibiotic. For example, one or more infections in a subject can be treated according to a method of the present disclosure by administering to the subject at least one ADAMTS4 inhibitor, at least one antibiotic, and one or more antiviral therapeutics, wherein the one or more antiviral therapeutics is administered about 5 min, 10 min, 15 min, 20 min, 25 min, 30 min, 45 min, 1 h, 1.5 h, 2 h, 2.5 h, 3 h, 3.5 h, 4 h, 4.5 h, 5 h, 5.5 h, 6 h, 7 h, 8 h, 9 h, 10 h, 11 h, 12 h, 18 h, 24 h, 30 h, 36 h, 42 h, 48 h, 54 h, 60 h, 72 h, 96 h, 5 days, 6 days, 1 week, 2 weeks, 3 weeks, or 4 weeks subsequent to administering the ADAMTS4 inhibitor and/or the antibiotic. Alternatively, the at least one ADAMTS4 inhibitor, the at least one antibiotic, and the one or more antiviral therapeutics may be administered concomitantly. For example, one or more infections in a subject can be treated according to a method of the present disclosure by administering to the subject at least one ADAMTS4 inhibitor, at least one antibiotic, and one or more antiviral therapeutics concomitantly.

In some instances, a method of treatment described hereinabove is repeated. For example, one or more methods of treatment described hereinabove can be repeated daily, once every 2 days, once every 3 days, once every 4 days, once every 6 days, once every week, once every 2 weeks, once every 3 weeks, once every 4 weeks, once every month, once every 2 months, once every 3 months, once every 4 months, once every 5 months, once every 6 months, once every 7 months, once every 8 months, once every 9 months, once every 10 months, once every 11 months, or once every year.

Administration and Dosage

Methods of treatment provide in the present disclosure may encompass administering at least one ADAMTS4 inhibitor, at least one antibiotic, and/or a pharmaceutical composition to a subject by different modes. Such modes of administration are well known to those skilled in the art and include, but are not limited to, oral administration, transdermal administration, administration by inhalation, nasal administration, topical administration, intravaginal administration, ophthalmic administration, intra-aural administration, intracerebral administration, rectal administration, sublingual administration, buccal administration and parenteral administration. In particular, parenteral administration includes, but is not limited to, injectable such as intravenous administration, intra-arterial administration, intramuscular administration, and subcutaneous administration. Administration can be continuous or intermittent. A preparation (e.g., a preparation containing at least one ADAMTS4 inhibitor, at least one antibiotic, and/or a pharmaceutical composition) a can be administered therapeutically, such as administered to treat an existing infection, disease or condition. A preparation can also be administered prophylactically, such as administered for prevention of an infection, disease, or condition.

The therapeutically effective amount or dosage of the at least one ADAMTS4 inhibitor, the at least one antibiotic, and/or a pharmaceutical composition described hereinabove can vary within wide limits. Such a dosage is adjusted to the individual requirements in each particular case including the specific ADAMTS4 inhibitor, antibiotic, and/or pharmaceutical composition being administered, the route of administration, the condition being treated, as well as the subject being treated. In general, in the case of oral or parenteral administration to adult human subjects weighing approximately 70 Kg or more, a daily dosage of about 5-10,000 mg, or more (e.g., about 10-10,000 mg, 25-7,500 mg, 50-5,000 mg, 75-2,500 mg, 100-1,000 mg, 150-750 mg, 200-500 mg, or more, such as about 5 mg, 10 mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1500 mg, 2000 mg, 2500 mg, 3000 mg, 3500 mg, 4000 mg, 4500 mg, 5000 mg, 5500 mg, 6000 mg, 6500 mg, 7000 mg, 7500 mg, 8000 mg, 8500 mg, 9000 mg, 9500, 10,000 mg, or more) of the ADAMTS4 inhibitor and/or the antibiotic should be appropriate, although the upper limit may be exceeded. The daily dosage can be administered as a single dose or in divided doses, or for parenteral administration, as a continuous infusion. Single dose can contain such amounts or submultiples thereof of the ADAMTS4 inhibitor, the antibiotic, and/or the composition to make up the daily dose. The dosage can be adjusted by the individual physician in the event of any contraindications. Dosage can vary, and can be administered in one or more dose administrations daily, for one or several days.

Infection

The present disclosure provides compositions and methods for treating one or more infections in a subject in need thereof. In some instances, the infection is a respiratory infection, such as an infection of one or more of nose, sinuses, mouth, pharynx, larynx, trachea, and lungs. In certain instances, a respiratory infection that can be treated by the compositions and methods of the present disclosure is an upper respiratory infection, such as an infection of one or more of nose, sinuses, mouth, and pharynx. Examples of upper respiratory infection include, but are not limited to, common cold (head cold), mild flu, tonsillitis, laryngitis, and sinus infection. Additionally, or alternatively, a respiratory infection that can be treated by the compositions and methods of the present disclosure is a lower respiratory infection, such as an infection of one or more of larynx, trachea, and lungs. Examples of lower respiratory infection include, but are not limited to: (i) viral infections, such as swine flu, avian flu, influenza, coronavirus infection, and viral pneumonia; and (ii) bacterial infections, such as whooping cough and tuberculosis. In particular, provided herein are compositions and methods for treating one or more lower respiratory infections in a subject in need thereof.

In specific embodiments, a respiratory infection that can be treated by the compositions and methods of the present disclosure is swine flu or H1N1. For example, swine flu or H1N1 caused by influenza A virus can be treated by the compositions and methods described herein.

Additionally, or alternatively, a respiratory infection that can be treated by the compositions and methods of the present disclosure is avian flu or bird flu. For example, avian flu or bird flu caused by the LPAI (low pathogenic avian flu) H7N9 variant of the influenza A virus and/or HPAI (high pathogenic avian flu) H5N1 variant of the influenza A virus can be treated by the compositions and methods described herein.

Additionally, or alternatively, a respiratory infection that can be treated by the compositions and methods of the present disclosure is an infection caused by non-polio enterovirus. For example, hand, foot, and mouth disease caused by non-polio enterovirus can be treated by the compositions and methods described herein.

Additionally, or alternatively, a respiratory infection that can be treated by the compositions and methods of the present disclosure is seasonal influenza or flu. For example, flu in children and flu in adults caused by influenza A or B viruses can be treated by the compositions and methods described herein.

Additionally, or alternatively, a respiratory infection that can be treated by the compositions and methods of the present disclosure is viral pneumonia. For example, viral pneumonia caused by influenza A or B viruses, respiratory syncytial virus (RSV), parainfluenza, and/or adenovirus can be treated by the compositions and methods described herein.

Additionally, or alternatively, a respiratory infection that can be treated by the compositions and methods of the present disclosure is bronchitis or chest cold. Bronchitis that can be treated by the compositions and methods of the present disclosure may be acute bronchitis or chronic bronchitis. For example, acute bronchitis caused by a virus that passes to lung following an upper respiratory infection can be treated by the compositions and methods described herein.

Additionally, or alternatively, a respiratory infection that can be treated by the compositions and methods of the present disclosure is common cold or head cold. For example, common cold caused by an adenovirus can be treated by the compositions and methods described herein.

Additionally, or alternatively, a respiratory infection that can be treated by the compositions and methods of the present disclosure is a coronavirus infection. In certain embodiments, severe acute respiratory syndrome (SARS) caused by coronavirus SARS-CoV can be treated by the compositions and methods described herein. Additionally, Middle East respiratory syndrome (MERS) caused by coronavirus MERS-CoV can be treated by the compositions and methods described herein. Additionally, Coronavirus Disease 2019 (COVID-19) caused by coronavirus SARS-CoV-2 can be treated by the compositions and methods described herein.

Additionally, or alternatively, a respiratory infection that can be treated by the compositions and methods of the present disclosure is whooping cough or pertussis. For example, whooping cough or pertussis caused by the bacterium *Bordetella pertussis* can be treated by the compositions and methods described herein.

Additionally, or alternatively, a respiratory infection that can be treated by the compositions and methods of the present disclosure is bacterial pneumonia. For example, pneumonia caused by *Streptococcus pneumoniae, Haemophilus influenzae, Mycobacterium tuberculosis*, and/or *Mycoplasma pneumoniae* can be treated by the compositions and methods described herein.

Therapeutic Effect

The present disclosure provides compositions and methods for treating, preventing and/or alleviating one or more infections described hereinabove. For example, the compositions and methods described herein can treat, prevent and/or alleviate one or more symptoms and/or complications associated with an infection, such as a respiratory infection.

In some aspects, the compositions and methods described herein can treat one or more infections. For example, compositions and methods of the present disclosure can cure, suppress, reduce, alleviate, and/or ameliorate one or more symptoms and/or complications associated with an infection described hereinabove. In some instances, compositions and methods of the present disclosure can reduce inflammation, immune cell infiltration, and/or tissue damage associated with the infection. For example, compositions and methods of the present disclosure can reduce inflammation, immune cell infiltration, and/or lung tissue damage associated with a respiratory infection, such as a viral infection described hereinabove (e.g., influenza). In certain instances, compositions and methods of the present disclosure can reduce mRNA and/or protein expression of one or more inflammatory cytokines or chemokines. For example, compositions and methods of the present disclosure can reduce mRNA and/or protein expression of TNFA and MCP-1.

Alteration of symptoms and/or complications as a result of treatment can be measured relative to any suitable control. For example, alteration of symptoms and/or complications can be measured relative to the frequency, severity, duration, or number of symptoms and/or complications experienced by the same subject prior to initiating the treatment. In other embodiments, alteration of symptoms and/or complications can be measured relative to the frequency, severity, duration, or number of symptoms and/or complications experienced by a different subject, or group of subjects with like symptoms and/or complications, who do not receive the treatment, such as who do not receive a composition or treatment described hereinabove. In some embodiments, the degree of improvement is at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. For example, compositions and methods of the present disclosure can reduce inflammation, immune cell infiltration, and/or tissue damage associated with an infection, such as a respiratory infection described hereinabove, by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control.

In some aspects, the compositions and methods described herein can prevent and/or delay the onset of symptoms and/or complications associated with an infection described hereinabove. For example, compositions and methods of the present disclosure can prevent and/or delay the onset of symptoms and/or complications associated with an infection described hereinabove. Prevention or delay in onset of symptoms and/or complications as a result of treatment can be measured relative to any suitable control. For example, prevention or delay in onset of symptoms and/or complications can be measured relative to the onset of symptoms and/or complications experienced by a different subject, or group of subjects with like symptoms and/or complications, who do not receive the treatment, such as who do not receive a composition or treatment described hereinabove. In some embodiments, the delay in onset of symptoms and/or complications is at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control. For example, compositions and methods of the present disclosure can delay the onset of symptoms and/or complications associated with an infection, such as a respiratory infection described hereinabove, by at least 5%, such as, at least 5%, 10%, 15%, 20%, 25%, 30%, 35%, 40%, 45%, 50%, 55%, 60%, 65%, 70%, 75%, 80%, 85%, 90%, 95%, 99% or more, as determined relative to a suitable control.

Subject

The present disclosure provides compositions and methods for treating one or more infections in a subject in need thereof. In some embodiments, a subject that can be treated by the compositions and methods of the present disclosure is a mammal, including, but not limited to, a human, a non-human mammal, a non-human primate, a primate, a laboratory animal, a mouse, a rat, a hamster, a cat, and/or a dog. In certain embodiments, a subject that can be treated by the compositions and methods of the present disclosure is a human subject. In particular, a subject that can be treated by the compositions and methods of the present disclosure is a patient, such as a human subject who shows one or more symptoms and/or complications associated with one or more infections described hereinabove. Additionally, or alternatively, a subject that can be treated by the compositions and methods of the present disclosure can be a patient, such as a human subject who has been diagnosed with one or more infections described hereinabove. Additionally, or alternatively, a subject that can be treated by the compositions and methods of the present disclosure can be a patient, such as a human subject who is under the treatment of a clinician, e.g., physician for one or more infections described hereinabove. A subject can be male or female.

In certain embodiments, a subject that can be treated by the compositions and methods of the present disclosure is a human subject who is at a risk of developing a secondary bacterial infection. Examples of secondary bacterial infection include, but are not limited to infections caused by *Streptococcus pneumoniae, Haemophilus influenzae, Staphylococcus aureus, Streptococcus pyogenes*, and/or *Moraxella catarrhalis*. For example, a subject that can be treated by the compositions and methods of the present disclosure can be a human subject who: (i) shows symptom(s) and/or complication(s) of one or more respiratory infections described hereinabove, has been diagnosed with one or more respiratory infections described hereinabove, and/or is under the treatment of a clinician for one or more respiratory infections described hereinabove; and (ii) is at a risk of developing a secondary bacterial infection, such as an infection caused by *Streptococcus pneumoniae, Haemophilus influenzae, Staphylococcus aureus, Streptococcus pyogenes*, and/or *Moraxella catarrhalis*. Additionally, or alternatively, a subject that can be treated by the compositions and methods of the present disclosure can be a human subject who shows one or more symptoms of and/or is diagnosed with a secondary bacterial infection. For example, a subject that can be treated by the compositions and methods of the present disclosure can be a human subject who: (i) shows symptom(s) and/or complication(s) of one or more respiratory infections described hereinabove, has been diagnosed with one or more respiratory infections described hereinabove, and/or is under the treatment of a clinician for one or more respiratory infections described hereinabove; and (ii) shows one or more symptoms of and/or is diagnosed with a secondary bacterial infection, such as an infection caused by *Streptococcus pneumoniae, Haemophilus influenzae, Staphylococcus aureus, Streptococcus pyogenes*, and/or *Moraxella catarrhalis*.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

The Examples below are merely illustrative, and are not intended to limit the scope of the disclosure provided herein in any way.

Example 1. Materials and Methods

Mice

B6.129P2-Adamts4tm1Dgen/J (ADAMTS-4−/−) mice were obtained from Jackson Laboratories. These mice were back-crossed with C57BL6/J mice for at least 10 generations to generate congenic ADAMTS-4−/− and ADAMTS-4+/+ mice.

Single-Cell RNA Sequencing

Whole lungs were collected from murine pathogen-free C57BL6/J mice (Taconic Biosciences) at 0, 1, 3, 6, and 21 days after initial infection. Four or five mice for each time point were infected with 2500 EID50 of mouse-adapted A/Puerto Rico/8/1934 (PR8) intranasally in 30 μL of 1×PBS 610. Lungs were perfused with 10 mL of cold 1×PBS injecting into the right ventricle of the heart and then minced and digested in lung digestion buffer containing 400 U/mL of Collagenase I (Worthington Biochemical Corporation) and 50 U/ml of DNaseI (ThermoFisher) in Hanks Balanced Salt Solution (HBSS) for 75 minutes at 37 degrees C. Digested lungs were filtered through a 100 μm cell strainer and washed with HBSS. Red blood cell lysis was performed and cells were resuspended at $1\times10^6$ cells/mL. Cells were incubated with Ghost Dye Violet 510 (Tonbo) (1:100 dilution) and APC anti-mouse CD45.2 (clone 104, Biolegend) (1:100 dilution) for 30 minutes at room temperature. Live, CD45− cells were sorted into 1.7 mL microfuge tubes and then centrifuged at 400×g for 5 minutes. Cells were then incubated with PE anti-mouse H-2 antibody (clone M1/42, Biolegend) for 30 minutes on ice.

Human lung biopsy samples from de-identified, deceased patients were obtained through the National Disease Research Interchange (NDRI). Cause of death for these patients was unrelated to respiratory tract infection or lung damage, and patients did not have a history of tobacco use or lung cancer. Fresh 5 cm×5 cm×5 cm lung biopsy samples were minced and digested in 400 U/ml of Collagenase I (Worthington Biochemical Corporation) and 50 U/ml of DNaseI (ThermoFisher) in Hanks Balanced Salt Solution (HBSS) for 90 minutes at 37 degrees. Lung samples were first filtered through sterile gauze and then through 100 μm cells strainer and washed with HBSS, and red blood cell lysis was performed. Single cells suspensions of total lung cells were frozen in freeze media (90% FBS/10% DMSO) at a concentration of $5\times10^6$ cells/mL. For scRNAseq using 10× Genomics, vials of cells were thawed and incubated with Ghost Dye Violet 510 (Tonbo) (1:100 dilution) and APC anti-human CD45 (1:200) for 30 minutes at room temperature. Live, CD45− cells and live, CD45+ cells were sorted into 1.7 mL microfuge tubes and then centrifuged at 400×g for 5 minutes. Following sorting, cells were incubated with PE anti-human 32 microglobulin antibody for 30 minutes on ice.

For both mouse and human lung samples, cells were washed three times and then incubated with custom-designed hashtag oligos (HTO) conjugated to anti-PE antibodies (Thunder-Link PLUS Oligo Conjugation System, Expedeon) unique for each individual mouse. After incubation, mouse-specific cells were washed three times and then pooled within each time point. ~25,000 cells per sample were loaded onto the Chromium controller (10× Genomics) to partition single cells into gel beads. Single cell transcriptomic libraries were generated using the 5' Gene Expression Kit (V2, 10× Genomics) according to the manufacturer's instructions with the addition of primers to amplify HTOs during cDNA amplification. Sequencing was performed on the Illumina NovaSeq to generate approximately 500M reads per sample.

Single-Cell Gene Expression Analyses

10× gene expression data were first processed using CellRanger (v3.0.2, 10× Genomics). Human data was processed using version 3.0.0 of the GRCh38 10× reference, whereas mouse data was processed using the mm10 reference altered to include the PR8 influenza genome. CellRanger was then used to aggregate species-specific samples, normalizing by the number of mapped reads per identified cell. Normalized feature-barcode matrices including both gene expression and HTO counts were then imported into Seurat (v3.0.0.900) for downstream analysis, as described, for example, by Stuart et al. (Cell 177:1888-1902.e21 (2019)).

Data were first filtered by excluding any gene that was not present in at least 0.10% of total called cells and then by excluding cells that exhibited extremes in the species-specific distributions of: the number of genes expressed (mouse: <100 or >5,550; human: <100 or >4,500), the number of mRNA molecules (mouse: >30,000; human: >20,000), or the percent of expression owed to mitochondrial genes (mouse and human: >7.5%). Gene expression counts were log-normalized using a scaling factor of 1e4, variable features targeted for downstream analysis were identified using the 'vst' method with default parameters, and cell cycle scores were generated using for each cell using markers identified elsewhere (Tirosh et al., *Science* 352:189-196 (2016)).

Gene expression was then scaled to regress out the effects of total transcript expression, percent of mitochondrial expression, and cell cycle scores. For first-pass analyses of entire datasets, we selected principal components (PCs) visually using an elbow plot of the PC standard deviations (mouse: 25; human: 19). These PCs were then used for t-SNE dimensionality reduction and cell clustering with Seurat's shared nearest neighbor modularity algorithm in order to broadly characterize the cell types in the entirety of each sample. Individual cell subsets were annotated using known markers from the literature.

For more detailed analyses of fibroblast populations, we generated a subset of the identified fibroblast clusters, identified the top variable features within this subset, and re-scaled that data as described above. For the mouse fibroblast data, we also regressed out the effects of days post infection (DPI) in order to more precisely characterize the variance among fibroblasts subsets and distinguish cellular responses to experimental infection. After re-conducting Principal Component Analysis, PCs were scored for significance (FDR-adjusted p-value<0.05) using random permutations as implemented in Seurat. Differential gene expression was assessed among clusters for all genes expressed in at least one percent of cells within a cluster using a generalized linear hurdle model that incorporates both expression frequency and abundance (Finak et al., *Genome Biology* 16 (2015)). For pairwise cluster comparisons of interest, genes were then ranked as a function of the product of their average log fold change, the absolute value of the difference in percent expression, and the inverse of the scaled, FDR-adjusted p-value. These gene rank lists were then analyzed using preranked Gene Set Enrichment Analysis (Subramanian et al., *Proc Natl Acad Sci* 102: 15545-15550 (2005)).

High-Throughput qPCR Using Fluidigm Biomark

For in vitro stimulation of primary murine lung fibroblasts, fibroblasts were isolated from C57BL6/J (Rifkin Lab, NYU Protocol). Lungs were collected, minced, and then digested in lung digestion buffer containing 0.1% Collagenase I (Worthington Biochemical Corporation) and 2.4 U/ml dispase (Thermo Fisher) for 90 minutes at 37 degrees C. Digested lungs were filtered through a 100 μm cells strainer and then washed with 15 mL of 0.05 M EDTA in 1×PBS. Cells were centrifuged at 400×g for 10 minutes and then re-suspended in complete Dulbecco's Modified Eagle Medium (cDMEM) and plated in a T75 tissue-culture flask (Corning). For cytokine and virus stimulations, $2\times10^5$ cells were plated in each well of a 24-well plate 24 hours prior to stimulation. Fibroblasts were stimulated with the following murine cytokines: IL-1B (10 ng/mL), IL-1A (10 ng/mL), IL-33 (10 ng/mL), IL-18 (10 ng/mL), TNFA (200 ng/mL), IFNA (1000 U/mL), IL-6 (40 ng/mL), TGFB (2 ng/mL), IL-17A (50 ng/mL), IL-27 (50 ng/mL), and GM-CSF (40 ng/mL). For the virus stimulations, cells were infected at a multiplicity of infection (MOI) of 2. Virus inoculum was incubated with the cells for 1 hour at 37 degrees C. The following viruses were used for the stimulations: A/Puerto Rico/8/1934 (PR8), A/California/04/2009 (CA09), and A/Perth/16/09 (Perth). The supernatant was removed, and cells were washed three times with cDMEM. The wells were replenished with 1 ml of cDMEM, and the cells were incubated at 37 degrees C. for 24 hours. To collect bronchoalveolar lavage (BAL) fluid, a catheter was inserted into the trachea, and 3 ml of 1×PBS was used to wash the lungs. BAL fluid was centrifuged at 400×g for 5 minutes to pellet cells, and then the cells were resuspended in 350 μl Trizol reagent.

Normal human bronchial epithelial cells (NHBEs) were plated in 24-well transwell plates (Corning) and cultured in Bronchial Epithelial Basal Medium (BEBM) (Lonza) supplemented with bovine pituitary extract, insulin, hydrocortisone, gentamicin/amphotericin, transferrin, triiodothyronine, epinephrine, epidermal growth factor, and retinoic acid until wells were confluent and cells formed tight junctions. Supernatant was then removed from the apical side of the transwell and cells were taken into the air-liquid interface until cells started producing mucus. NHBEs were then stimulated with the following human cytokines adding each factor to media in the basal chamber: IL-1B (10 ng/mL), IL-1A (10 ng/mL), IL-33 (10 ng/mL), IL-18 (10 ng/mL), TNFA (200 ng/mL), IFNA (1000 U/mL), IL-6 (40 ng/mL), TGFB (2 ng/mL), IL-17A (50 ng/mL), IL-27 (50 ng/mL), and GM-CSF (40 ng/mL). For virus stimulations, cells were infected at a multiplicity of infection (MOI) of 2. Virus inoculum was incubated with the cells in the apical 715 chamber for 1 hour at 37 degrees C. The supernatant was removed, and cells were washed three times with BEBM, and incubated at 37 degrees C. for 24 hours. Normal human bronchial fibroblasts (NHBFs) (Matek) were plated in 24-well plates at a density of $2\times10^5$ cells/well and cultured in cDMEM. NHBFs were stimulated with the cytokines and viruses listed above. Following incubation, the supernatant was removed and cells were collected in 350 μl Trizol Reagent (Thermo Fisher). RNeasy spin columns (Qiagen) were then used to isolate RNA from the samples according to the manufacturer's instructions. Following RNA isolation, the amount of RNA input was normalized (200 ng), and cDNA was generated using the iScript cDNA synthesis kit (Biorad). cDNA was then prepared for quantitative polymerase chain reaction (qPCR) using the Fluidigm Biomark (Fluidigm). Exon-spanning qPCR primers were designed to target a panel of 96 ECM-related genes.

For whole lung homogenates from mice, lungs were collected at 0, 1, 3, 6, 9, 12, 15, 30, and 40 days after infection. C57BL6/J mice were infected with 2500 EID50 PR8. Whole lungs were dissected and homogenized in 750 μl Trizol reagent using the TissueLyser II (Qiagen). RNA was isolated according to the manufacturer's protocol.

ADAMTS-4−/− and ADAMTS-4+/+ Survival Experiments

Mice were infected intranasally with 6000 EID50 of PR8 in 30 μl 1×PBS after anesthetizing with 2,2,2-tribromoethanol by intraperitoneal (i.p.) injection. Following infection, mice were monitored twice daily and weight was recorded. Mice were euthanized if they become severely moribund based on body index score and substantial weight loss (Sanders et al., *AJP: Lung Cellular and Molecular Physiology* 304: L481-L488 (2013)).

Plaque Titers

BAL fluid was used to obtain viral titers inoculating Madin-Darby Canine Kidney (MDCK) cells. MDCKs were plated in six-well tissue culture plates at a density of $4\times10^5$ cells/well. Twenty-four hours after plating, cells were washed three times with 1×PBS and then incubated with 1 mL of BAL fluid, after performing six 10-fold dilutions in serum-free MEM. Cells were incubated with inoculum for 10 minutes at 4 degrees Celsius and then for 50 minutes at 37 degrees Celsius. Inoculum was removed and 3 mL of MEM containing 0.9% agarose and 1 mg/ml of L-1-tosylamido-2phenylethyl chloromethyl ketone-treated (TPCK) trypsin was overlaid onto the cell monolayer. Plates were then incubated at 37 degrees for 72 hours, and then plaques were counted after staining the cells with crystal violet.

Histology and Morphometry Viral Spread Analysis

Lungs were dissected at 3 and 6 days after infection with 2500 EID50 of PR8. Lungs were inflated with 1 mL of 10% neutral-buffered formalin, and then placed in a 15 mL conical tube containing 3 mL more of formalin. Lungs were incubated in formalin at room temperature for at least 72 hours to ensure complete fixation of the tissue. Lungs were embedded in paraffin blocks and then sectioned onto glass slides. Serial tissue sections were stained with hematoxylin and eosin (H&E) for histology or immunohistochemical labeling of viral antigen was completed by using a primary goat polyclonal antibody (US Biological, Swampscott, MA) against influenza A, USSR (H1N1) at 1:1000 and a secondary biotinylated donkey anti-goat antibody (catalog number sc-2042; Santa Cruz Biotechnology, Santa Cruz, CA) at 1:200 on tissue sections subjected to antigen retrieval for 30 minutes at 98° C. The extent of virus spread was quantified by first capturing digital images of whole-lung sections stained for viral antigen using an Aperio ScanScope XT Slide Scanner (Aperio Technologies, Vista, CA) and then manually outlining fields with the alveolar areas containing virus antigen-positive pneumocytes. The percentage of each lung field with infection/lesions was calculated using the Aperio ImageScope software. For histologic grading of lesions, a pathologist blinded to treatment group identity evaluated pulmonary lesions in H&E-stained histologic sections and assigned scores based on their severity and extent as follows: 0=no lesions; 1=minimal, focal to multifocal, barely detectable; 15=mild, multifocal, small but conspicuous; 40=moderate, multifocal, prominent; 80=marked, multifocal coalescing, lobar; 100=severe, diffuse, with extensive disruption of normal architecture and function.

Assessment of CD8+ T Cell Responses

In order to assess immune cell populations by flow cytometry, whole lungs were dissected, minced, and incubated with spleen dissociation media (STEMCELL) for 30 minutes at 37 degrees C. Red blood cell lysis was performed, and cells were washed with HBSS and counted using a Vi-CELL XR cell counter (Beckman Coulter). For ex vivo stimulation and intracellular cytokine staining, $1\times10^6$ total lung cells were plated in a 96-well plate for each condition. Cells were stimulated with Cell Stimulation Cocktail (Biolegend), containing PMA/ionomycin and Brefeldin A, at a dilution of 1:500 or with influenza peptides at a concentration of 1 μM for 4 hours. Following stimulation, cells were washed and then incubated with Fc block (Biolegend) at a dilution of 1:100 for 10 minutes at room temperature. For surface staining, cells were then washed and incubated in 100 μl of FACS buffer (1% FBS/1 mM EDTA in 1×PBS) containing Live/Dead Aqua (1:100), APC anti-mouse CD45.2 (1:100), FITC anti-mouse CD3 (1:100), BV650 anti-mouse CD8 (1:200), and APC/Cy7 anti-mouse CD4 (1:200) for 30 minutes at room temperature. For intracellular staining, cells were fixed and membranes permeabilized by incubating in 100 μl fixation/permeabilization solution (BD Biosciences) for 20 minutes on ice. Cells were washed with permeabilization buffer and then incubated with PE/Cy7 anti-mouse IFNG (1:100) for 30 minutes on ice.

For IAV peptide:MHC tetramer staining, $1\times10^6$ total lung cells were plated in a 96-well plate for each sample. Cells were incubated with APC $PB1_{703-711}$ tetramer (1:750), PE $PA_{224-233}$ tetramer (1:750), and BV785 $NP_{366-375}$ tetramer (1:250) for 1 hour on ice. Then, cells were surface stained with FITC anti-mouse CD3 (1:100), BV650 anti-mouse CD8 (1:200), APC/Cy7 anti-mouse CD4 (1:200) for 30 minutes on ice.

Lung Tissue Immunofluorescence

Lungs were dissected 9 days after infection with 2500 EID50 of PR8. Lungs were inflated with 1 mL of fixative containing 2% paraformaldehyde, 0.1% Triton-100 and 1% DMSO and then transferred to a 15 mL conical tube containing 3 mL of fixative for 24 h prior to cryoprotection with 30% sucrose in PBS for an additional 24 h. Tissues were cryosectioned at 10 μm thickness and blocked in buffer comprised of PBS containing 2% bovine serum albumin and 5% donkey serum. Tissues were stained overnight in blocking buffer containing 4 μg/mL rat anti-CD3 (Biolegend, clone 17A2), and 4 μg/mL rabbit anti-mouse versican GAG beta domain (Millipore Sigma, AB1033). Sections were washed in PBS priorto incubation with CF488-conjugated donkey anti-rat IgG (Biotium, 20027, lot 16C0301, 2

μg/mL), CF568-conjugated donkey anti-rabbit IgG 804 (Biotium, 20098, lot 19C0110, 2 μg/mL) and DAPI [10 uM] for 1 hr at RT. Slides were washed with PBS and mounted with prolong diamond hardset mounting medium (ThermoFisher). High resolution images were acquired using a Marianis spinning disk confocal microscope (Intelligent Imaging Innovations) equipped with a 40×1.3NA Plan-Neofluar objective, 405 nm, 488 nm and 561 nm laser lines and Prime 95B CMOS camera (Photometrics), and analyzed using Slidebook software (Intelligent Imaging Innovations). For quantification of CD3+ cells, 3-4 fields of view in the areas of tissue remodeling were collected for each lung.

Lung Function Test

For lung function studies, mice were infected with 2500 EID50 of PR8. At 10 days post-infection, mice were anesthetized with 2,2,2-tribromoethanol by intraperitoneal (i.p.) injection and tracheal tube was inserted. Airway resistance and dynamic lung compliance was measured using the Buxco Finepointe Resistance and Compliance system (Data Sciences International). Mice were mechanically ventilated at a rate of 140 breaths/minute. Five methacholine challenges were performed at doses of 1.5625, 3.125, 6.25, 12.5, and 25 mg/ml, administering the methacholine in 0.010 ml of PBS. Following each methacholine challenge, resistance and compliance were measured for 3 minutes allowing the mice to recover for 1 minute after each measurement. Measurements for resistance and compliance were averaged over the 3-minute measurement period for each methacholine challenge and baseline measurements.

Cytokine Bead Arrays

Cytokine levels in lung tissue homogenates were measured using LEGENDplex cytokine bead arrays (Biolegend). Lungs were dissected from PR8-infected mice at 6 days post-infection and homogenized in 500 μl of PBS. Homogenized lung samples were centrifuged at 4,000×rpm for 10 minutes, and 25 μl of undiluted supernatant was tested in the assay. The assay was performed according to the manufacturer's instructions.

Human Cohorts

For the Guangzhou cohort, the study was approved by the ethics committee of the First Affiliated Hospital of Guangzhou Medical University (No: 2016-78), and informed consent was obtained from all patients or their guardians.

For the Taiwan cohort, the human subjects' protocol was reviewed and approved by the Johns Hopkins School of Medicine and the Chang Gung Memorial Hospital Institutional Review Boards (IRB00091667). This protocol allowed for the collection of residual bronchoalveolar lavage (BAL) and sputum samples that were initially collected for clinical purposes from influenza positive patients.

For statistical analysis, we operationally defined two groups of disease severity based on length of hospital stay and outcome (discharge or death). The 'moderate' group included patients who had a hospital stay of less than 20 days and were discharged from the hospital. The 'severe' group included patients who had a hospital stay greater than 20 days or died in the hospital. This severity determination was designed to have comparable numbers of patients in each group (28 moderate and 38 severe), and division into two groups reduced the amount of testing to retain statistical power.

Quantification of Matrix Protease and Cytokine/Chemokine Protein Levels in Human Samples Cytokine and chemokine levels were measured using Milliplex Human Cytokine/Chemokine Magnetic Bead Panel—Premixed 41-plex. MMP and TIMP protein levels were quantified using the following Milliplex bead-based multiplexed assay, Human MMP Magnetic Bead Panel 1 (MMP-3, MMP-12, MMP-13), Human MMP Magnetic Bead Panel 2 (MMP-1, MMP-2, MMP-7, MMP-9, MMP-10), and Human TIMP Magnetic Bead Panel 2 (TIMP-1, TIMP-2, TIMP-3, TIMP-4). ADAMTS-4 and ADAMTS-5 were measured using Duoset ELISA kits (R&D Systems).

Cytokine Correlation Matrices

Correlation matrices were generated using only the first sample obtained from each patient, with cytokines log 10 transformed. To control for potential effects of age, sample type, and day of sample collection (days after symptom onset; DAO), we computed partial pairwise spearman correlations and assessed their statistical significance using the R psych package (Revelle, *Procedures for Psychological, Psychometric, and Personality Research* [*R package psych*]. (Comprehensive R Archive Network (CRAN), 2019)). Correlations were visualized using the R corrplot package (Wei & Simko, *R package 'corrplot': Visualization of a Correlation Matrix*. (Github, 2017)), and correlations with p-values<0.05 after FDR adjustment were excluded.

Severity Analyses

To characterize the potential correlates of ADAMTS-4 abundance while controlling for the non-independence of data owed to time-series sampling of some patients, we used the lme4 R package (Bates et al., Fitting Linear Mixed-Effects Models Using lme4. *Journal of Statistical Software* 67 (2015)) to model log 10 ADAMTS-4 abundance as a function of severity, day of sample collection (DAO), and cohort, as well as the interactions thereof, with patient as a random effect. The car R package (Fox & Weisberg, *An R Companion to Applied Regression, Third Edition*. (Sage Publications, 2011)) was then used to assess the significance of model effects, and we verified the homoscedasticity of the residuals visually.

Data and Code Availability

All data and computer code presented in this study are available upon request.

Example 2. Single-Cell Gene Expression Profiling Identifies Distinct Antiviral and Tissue-Damage Responses in Fibroblasts During Severe Influenza Virus Infection The present study is directed to identifying mechanistic targets that alter the balance between pathogen clearance and immunopathology to improve outcomes following severe respiratory infections leading to acute respiratory distress syndrome (ARDS). Potential therapeutic targets that alter this balance include components of the lung extracellular matrix (ECM). The ECM provides structural support to the lung that is critical for its function and tissue-specific signals to coordinate immune responses to infection or injury. Studies to advance the mechanistic understanding of the immune stimuli that induce expression of ECM components, the cellular source of these proteins, and the effect on the lung ECM in vivo are needed to identify promising therapeutic targets that would limit immunopathology and lung injury.

The lung ECM is made up of hundreds of proteins with diverse functions, which include both structural components and matrix proteases that degrade or modify the ECM (Hynes & Naba, *Cold Spring Harbor Perspectives in Biology* 4:a004903-a004903 (2012)). Matrix proteases include two large gene families, matrix metalloproteinases (MMP) and A disintegrin and metalloproteinase with thrombospondin motifs (ADAMTS). Upon lung infection or injury, many matrix proteases are upregulated and extensively remodel the ECM, facilitating the migration of immune cells to sites of inflammation (Bonnans & Werb, *Nature Reviews Molecular Cell Biology* 15:786-801 (2014); Sorokin, *Immunology* 10:712-723 (2010)). In humans, concentrations of several MMPs, either in the respiratory tract or in the peripheral blood, have been associated with severe respiratory infection and ARDS (Guan, *J Infect Dis* 218:1238-1248 (2018); Hastbacka et al., *Anesthesia & Analgesia* 118:790-798 (2014); Kong et al., *PLoS ONE* 6:e22596 (2011); Pugin et al., *Crit Care Med* 27:304-312 (1999); Zinter et al., *Am J Respir Crit Care Med* 199:181-189 (2019)). Mouse models of severe respiratory infection have implicated immune cells, including both macrophages and neutrophils, and lung parenchymal cells (Talmi-Frank et al., *Cell Host Microbe* 20:458-470 (2016); Bradley et al., *PLoS Pathogens* 8:e1002641 (2012); Rojas-Quintero et al., *JCI Insight* 3, (2018)) in MMP production.

Non-immune lung cells, including epithelial and endothelial cells as well as fibroblasts, play the dual roles of coordinating immune responses to infection and directly mediating lung function (Iwasaki & Pillai, *Nature Reviews Immunology* 14:315-328 (2014)). Through their tissue remodeling activity, specific cell populations can influence the outcome of infection and long-term sequelae, as has been described for myofibroblasts and lung fibrosis (El Agha et al., *Cell Stem Cell* 21:166-177 (2017)). The role of lung stromal cell populations in coordinating host responses to an active respiratory infection has received relatively less attention than their role in the late-stage repair following pathogen clearance.

In the present study, a high-resolution cellular map of the CD45− compartment in the lung was generated over the course of severe Influenza A virus (IAV) infection in mice using single-cell gene expression profiling. The results are outlined in Examples 2-5. Among non-immune cells, fibroblasts were highly dynamic and displayed heterogeneity following IAV infection. Subsets of inflammatory lung fibroblasts were identified that emerged in response to infection and were characterized by expression of unique cytokine/chemokine and matrix protease modules that correspond to distinct antiviral and tissue-damage responsive pathways. Damage-responsive, extracellular matrix (ECM)-remodeling phenotypes in both human and mouse lung fibroblasts were induced by stimulation with IL-1 cytokines and TNFA.

In the mouse model of severe IAV infection, a single fibroblast-derived matrix protease, ADAMTS-4, was found to be a major driver of immunopathology and tissue damage resulting in compromised lung function. Analysis of matrix proteases and cytokines in lower respiratory tract samples from two human cohorts of severe influenza infections, including both seasonal and H7N9 avian influenza cases, showed that ADAMTS-4 grouped independently of most inflammatory mediators and correlated with disease severity. These data identify the exuberant activity of damage-responsive fibroblasts as a key driver of lung immunopathology and the matrix protease ADAMTS-4, a signature effector of this fibroblast population, as a promising therapeutic target to promote a tissue-tolerant environment preserving lung function and preventing progression to severe complications, including acute respiratory distress syndrome (ARDS).

At first, regulation of transcriptional profiles of 96 ECM-related genes was assessed in whole lung homogenates collected from IAV-infected mice at 0, 1, 3, 6, 9, 15, 30, and 40 days after infection using high-throughput qPCR. Genes included those encoding matrix metalloproteinases (MMP) and A disintegrin and metalloproteinase with thrombospondin motifs (ADAMTS) matrix proteases, ECM structural proteins, and inflammatory cytokines and growth factors known to be upregulated during influenza infection. Averaged transcriptional profiles in whole lungs demonstrated clear temporal regulation of groups of ECM-related genes over the course of severe IAV infection in mice (FIG. 1A). The top genes upregulated in response to infection followed three distinct temporal expression patterns: continuous expression during infection (Il6, Timp1, Adamts4, Mmp10), expression during the peak of infection and the peak inflammatory response (Il1b, Mmp14, Mmp3, Vcan), and late expression during tissue repair (Eln, Col3a1, Mmp12, Mmp7).

Figure 1B:
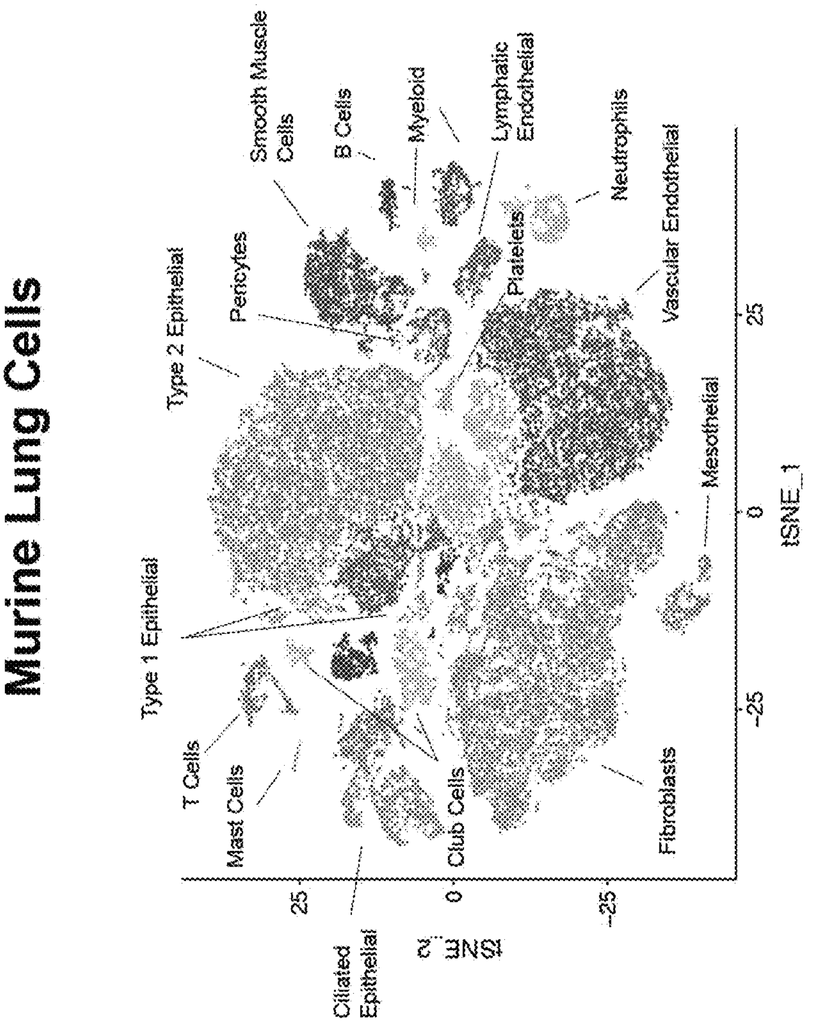

While transcriptional profiling of lung homogenates provided a global view of ECM-related gene expression over the course of infection, we next sought to generate a high-resolution map of cells that are involved in regulating these pathways at distinct stages of infection. Many of the ECM-related genes identified as upregulated in whole lung homogenates are known to be expressed by stromal cells in the lung. While there is extensive literature investigating the diversity of immune cells and their role in regulating the host response to IAV infection (Iwasaki & Pillai, *Nature Reviews Immunology* 14:315-328 (2014)), there is less information on the heterogeneity of non-hematopoietic cells and their role in the response to infection. Live, CD45− lung cells were sorted from mice 0, 1, 3, and 6 days after initial infection and single-cell gene expression profiling (scGEX) was performed. In total, 40,800 lung cells were sequenced from 19 individual mice with 4-5 animals per time point. Labeling individual mice with DNA-tagged antibodies indicated that single cell transcriptional profiles from biological replicates were consistent within time points. In agreement with previous reports (Cohen et al., *Cell* 175: 1031-1044.e18 (2018); Steuerman et al., *Cell Systems* 6:679-691.e4 (2018)), t-stochastic neighbor embedding (t-SNE) clustering identified three main populations of CD45− cells: epithelial cells, endothelial cells, and fibroblasts (FIG. 1B). Each of these three main cell types included multiple subpopulations that corresponded to phenotypically distinct cell subsets. In addition to host cell mRNA, we were able to sequence viral mRNA transcripts that mapped to the IAV genome. High levels of viral mRNA, indicative of productive infection, were primarily detected in type-I pneumocytes and to a lesser extent in ciliated epithelial cells and type-II pneumocytes. In contrast, cells with high levels of viral mRNA were rare among the endothelial and fibroblast populations.

Among the three main populations of CD45− cells, fibroblasts were particularly dynamic and heterogeneous, with multiple putative populations emerging following IAV infection. Unsupervised clustering of mesenchymal cells expressing the signature gene Col1a2 identified 19 groups of fibroblasts and smooth muscle cells with distinct transcriptional profiles. An overlay of the time point after infection demonstrated that while some populations of fibroblasts were present before and after infection (0, 1, 3, 5), other populations emerged in response to infection (4, 6, 8). In order to assess the biological pathways that were active in each of these fibroblast populations, we performed gene-set enrichment analysis (GSEA) comparing each cluster to a putative baseline cluster (5) that was present prior to infection and had relatively few differentially expressed genes compared to the entire dataset. Through GSEA, we identified at least three primary functional groups that broadly encompass the broad diversity of gene expression among all fibroblasts: resting, ECM-synthesizing, and inflammatory. ECM-synthesizing fibroblasts (ESFibs) were enriched for the myogenesis pathway and others involved in production of ECM structural proteins, but lacked inflammatory signatures, despite their emergence emerging specifically in response to infection. Inflammatory subpopulations had high expression of genes involved in type-I interferon, IL-6, and NFkB signaling, while resting fibroblasts lacked strong enrichment for pathways involved in either inflammatory responses or synthesis of ECM structural proteins. A minor fourth cluster of fibroblasts identified by consistent expression of Col13a1 exhibited concurrent signals of multiple gene signatures that distinguished otherwise distinct primary groups.

Within the inflammatory fibroblasts, we identified two distinct functional subgroups, the damage-responsive fibroblasts (DRFibs), and interferon-responsive fibroblasts (IRFibs). DRFibs were enriched for pathways involved in tissue-damage responses, including NFKB signaling, hypoxia, angiogenesis, and coagulation, whereas IRFibs were highly enriched for type-I-interferon-responsive pathways. Pairwise comparison of the two inflammatory subgroups emphasized the antiviral interferon phenotype of the IRFibs and the tissue-damage response of DRFibs, highlighting the distinct inflammatory programs of fibroblasts in response to different aspects of the infection.

Each of the infection-induced populations of fibroblasts expressed signature gene sets of cytokines/chemokines and ECM-related factors that underscored their distinct matrix building, matrix degrading, or antiviral profiles. ESFibs expressed ECM proteoglycans, including lumican and elastin, that contribute to the maintenance of lung structure. DRFibs expressed numerous matrix degrading proteases, including MMPs and ADAMTSs (Adamts4), and cytokines/chemokines associated with NFkB responses (IL6, Cxcl) that promote immune cell infiltration. IRFibs expressed genes involved in multiple facets of type-I interferon responses, including production of type-I interferons (Irf7), cytokine signaling (Ifnar2), and direct inhibition of viral replication (Bst2).

Figure 1C:
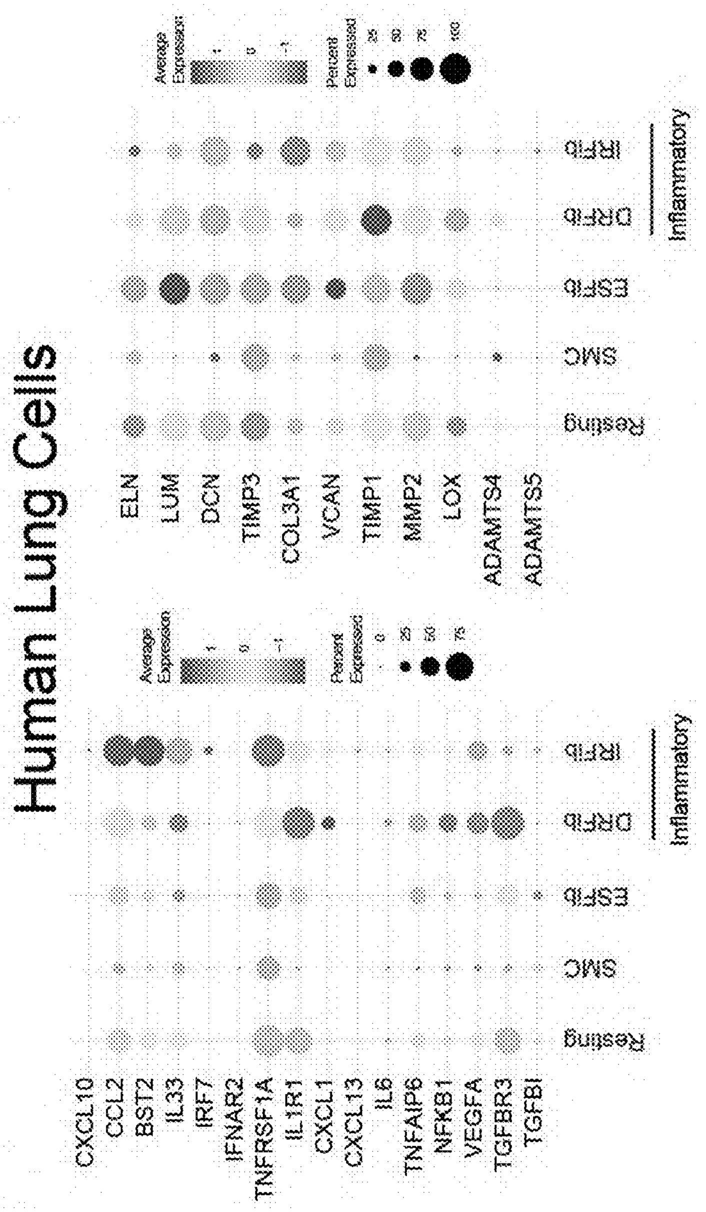

In order to investigate the broader relevance of these novel fibroblast populations outside of the murine model and determine their implications for human pulmonary health, we performed scGEX of cells from five human lung biopsies. Among human mesenchymal cells expressing COL1A2, we identified populations of fibroblasts analogous to those defined in mouse lungs. Distinct populations of fibroblasts were enriched for pathways involving ECM synthesis, NFkB signaling, and type-I interferon signaling, representing human ESFibs, DRFibs, and IRFibs, respectively. Moreover, these populations of fibroblasts had similar patterns of expression of inflammatory cytokines/chemokines and ECM-related genes that were identified for ESFibs (ELN, LUM), DRFibs (ADAMTS4, IL6) and IRFibs (IRF7, BST2) in mice (FIG. 1C).

Overall, scGEX of lung cells during IAV infection allowed us to resolve distinct inflammatory programs in fibroblasts that are induced in response to the viral infection itself (IRFibs) or to infection-associated damage (DRFibs). The extensive data obtained from the whole-lung mouse model of infection was particularly important for identifying expression-based cell subpopulations and characterizing subpopulation-specific changes in response to changes in microenvironment. Subsequent analysis of human lung tissue confirmed the taxonomic conservation of these distinct subpopulations between mice and humans.

Example 3. IL-1 Cytokines and TNFA Induce ECM Remodeling Pathways in Human Lung Fibroblasts After defining the fibroblast subpopulations that develop in response to influenza infection, we next sought to identify the upstream stimuli that promote distinct inflammatory phenotypes.

Although they are not productively infected, fibroblasts did express a wide range of cytokine/growth factor receptors, including receptors for type-I interferons, IL-1 cytokines, TNFA, TGFB, IL-17, and IL-6, that could allow them respond to virus-induced stimuli. Following our findings in mice, we stimulated human respiratory cells with a panel of cytokines and growth factors known to be upregulated during IAV infection and with IAVs representing currently circulating subtypes, HIN1 (PR8, CA09) and H3N2 (Perth). Normal human bronchial fibroblasts (NHBFs) and differentiated normal human bronchial epithelial cells (NHBEs) were stimulated with the indicated cytokines and viruses, and ECM-related gene expression was assessed by high-throughput qPCR. In vitro stimulated respiratory cells were also compared to cells isolated from influenza virus-infected patient nasal washes, which primarily contain infiltrating immune cells (Allen et al., *Nature Medicine* 23:975-983 (2017); Oshansky et al., *American Journal of Respiratory and Critical Care Medicine* 189:449-462 (2014)). The panel of ECM-related genes included those encoding inflammatory cytokines and corresponding cytokine receptors, ECM structural proteins (e.g. collagens, elastin, proteoglycans), and members of the MMP and ADAMTS matrix protease families. Hierarchical clustering of samples based on relative mRNA levels normalized to Actb demonstrated cell-type specific expression of subsets of ECM-related genes, in particular the MMP and ADAMTS matrix proteases.

Figure 2:
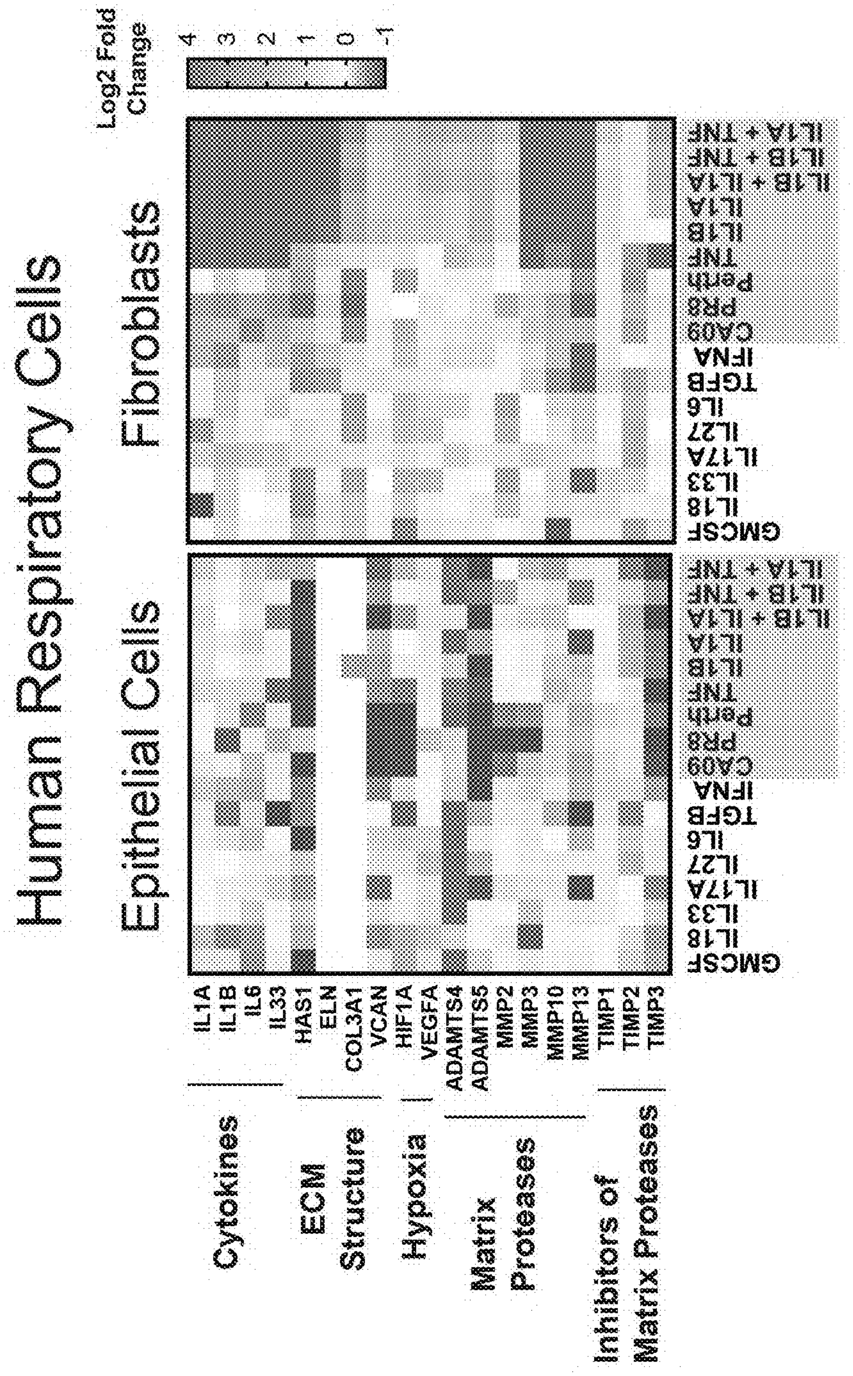
FIG. 2 provides data showing induction of extracellular matrix (ECM) remodeling pathways in human lung by IL-1 cytokines and TNFA.

With respect to ECM-related genes, epithelial cells were relatively unresponsive to cytokine stimulation (FIG. 2). In NHBEs, IFNA and virus stimulation led to modest upregulation of Mmp10, Mmp13, Timp1. In contrast, fibroblasts were highly responsive to stimulation with IL-1 cytokines and TNFA, and numerous genes encoding cytokines, ECM structural proteins, and matrix proteases were upregulated (FIG. 2). These genes included those associated with DRFibs (I16, Vegfa, Hif1a, Adamts4) and also IRFibs (I133, Vcan, Mmp3, Timp1). The magnitude of induction by IL-1 and TNFA varied widely across matrix proteases, with expression increasing 100-1,000-fold for a cluster of MMPs. These highly induced MMPs are located in the same chromosomal locus, which may be a site of open chromatin in fibroblasts allowing for robust induction. In general, the ADAMTS genes (including ADAMTS4 and ADAMTS5) were more tightly regulated, with a 2-10 fold change in mRNA levels.

Nasal wash cells from influenza-infected individuals had low levels of expression of ECM-related genes encoding both structural proteins and matrix proteases. Nasal wash cells and epithelial cells did exhibit high relative levels of Il1a, Il1b, and Tnf expression, indicating that these cells likely provide the immune signals to fibroblasts to regulate ECM-related gene expression. These results suggest a pathway of innate stimulation that is initiated by direct viral infection by epithelial cells, followed by cytokine secretion and amplification by recruited immune cells that results in the integration of these signals in inflammatory fibroblasts. These fibroblast populations can further amplify cytokine inflammatory signals. Crucially, they also produce key mediators of lung structural construction and degradation in a highly regulated manner, with the ADAMTS family showing a particularly refined regulatory profile based on upstream inflammatory input, cell differentiation status, and stage of infection.

Although matrix proteases act as networks to modify the ECM during lung injury, we sought to determine if any individual protease played a fundamental effector role underlying lung productive and nonproductive repair. We specifically focused these efforts on ADAMTS-4 for several reasons. Based on transcriptional profiling of whole lung homogenates, Adamts4 expression was induced early, by at least 24 hours after infection, and continued until the repair stage (FIG. 1A). Moreover, Adamts4 was identified as a signature gene of the DRFib response to infection (FIG. 1C) and was induced by stimulation with IL-1 cytokines and TNFA (FIG. 2). Furthermore, a major enzymatic target of ADAMTS-4, the lung proteoglycan versican (VCAN) (Kelwick et al., *Genome Biology* 16 (2015)), was induced following IAV infection on the transcriptional level (FIG. 1A).

Example 4. ADAMTS-4 Promotes Lethal Immunopathology and Tissue Resistance in a Model of Severe IAV Infection in Mice Next, to determine the contribution of ADAMTS-4 to the outcome of influenza infection, we challenged ADAMTS-4−/− (KO) and ADAMTS-4+/+(WT) mice with a lethal dose of IAV H1N1 A/Puerto Rico/8/1934 (PR8).

Figure 3A:
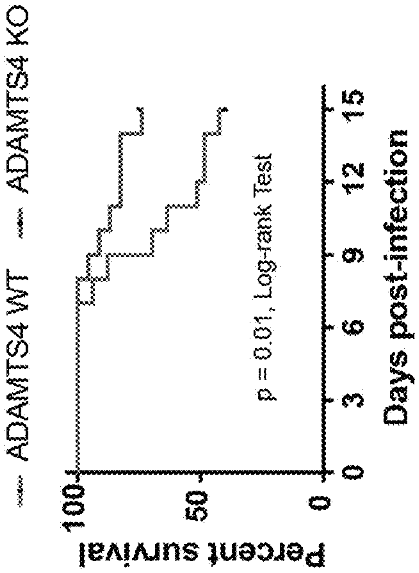
FIGS. 3A-3E provides data showing ADAMTS-4-mediated promotion of lethal immunopathology and tissue resistance in a model of severe Influenza A virus (IAV) infection in mice.

Although there was no significant difference in weight loss, ADAMTS-4−/− mice exhibited improved survival compared to ADAMTS-4+/+ controls (Log-Rank Test, p=0.01) (FIG. 3A). The improved survival in the ADAMTS-4−/− mice was independent of the viral burden in the lungs as determined by the percentage of the lung actively infected and by viral plaque titers in bronchoalveolar lavage (BAL) fluid and lung tissue. We also assessed cell-type specific infection in single cell suspensions of whole lungs by measuring IAV nucleoprotein (NP) positivity using flow cytometry; overall, there was not a significant difference between ADAMTS-4−/− and ADAMTS-4+/+ mice with respect to the percentage or number of total NP+ cells at 6 dpi. The percentage of NP+ epithelial cells, the main target cell of IAV, also did not differ between the two groups. In contrast, the percentage of NP+ monocytes was significantly lower in the ADAMTS-4−/− mice (0.37 vs. 0.20%, p=0.01), while there was a trend towards a lower percentage of NP+ fibroblasts (0.68 vs. 0.41%, p=0.09). Given that monocytes and fibroblasts are predominantly located on the interstitial or vascular side of the bronchioles and alveoli, these cell-type dependent differences in NP+ suggested compartmentalization of viral protein in the apical, epithelial layer of ADAMTS-4−/− lungs, consistent with degradation of ECM barriers due to ADAMTS-4 activity.

Figure 3B:
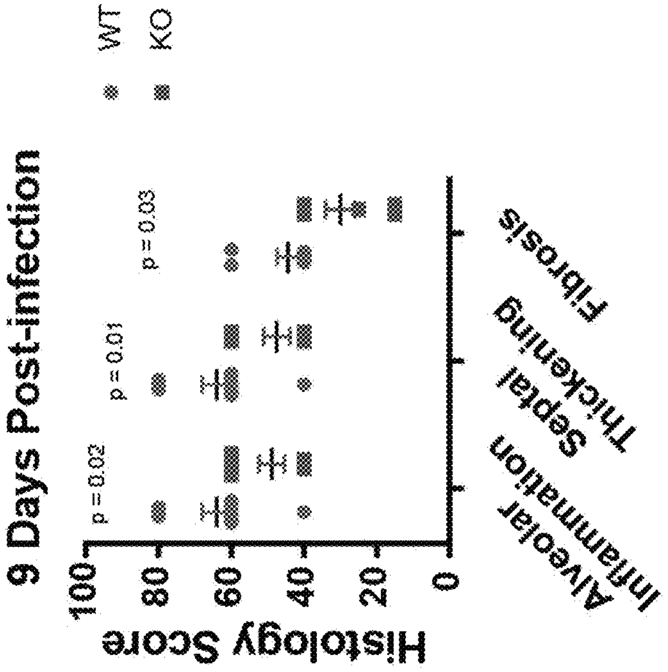

Evidence from both human cases and murine models of severe IAV infection indicates that lung tissue damage resulting from immunopathology is a major contributor to morbidity and mortality (Duan & Thomas, *Frontiers in Immunology* 7 (2016); La Gruta et al., *Immunology and Cell Biology* 85:85-92 (2007)). After infecting with a sublethal dose of IAV PR8, we assessed lung pathology in ADAMTS-4−/− and ADAMTS-4+/+ mice. ADAMTS-4−/− mice exhibited a marked decrease in immune cell infiltration, with significantly lower histological scores for alveolar inflammation. Compared to ADAMTS-4+/+ mice at 9 dpi, there was also evidence of reduced lung tissue damage in ADAMTS-4−/− mice, which exhibited significantly lower histological scores for alveolar septal thickening and fibrosis (FIG. 3B). Consistent with reduced immunopathology and tissue damage, ADAMTS-4−/− mice had less total protein in BAL fluid compared to ADAMTS-4+/+ controls (0.4 vs. 1.0 mg/ml, p=0.03). ADAMTS-4−/− mice also exhibited reduced expression of a number of inflammatory cytokines and chemokines, including TNFA and MCP-1, in lung tissue homogenates. Immunofluoresence imaging of lung sections demonstrated that a major ADAMTS-4 substrate, versican, accumulates in the lung following infection. Comparison of lungs from ADAMTS-4−/− and ADAMTS-4+/+ after IAV infection indicated that ADAMTS-4 deficient mice had higher levels of intact VCAN in areas of lung remodeling, highlighting changes to the lung ECM. In total, these results establish that ADAMTS-4 activity during severe IAV infection promotes immune cell infiltration into the lungs and contributes to loss of tissue integrity.

Figure 3C:
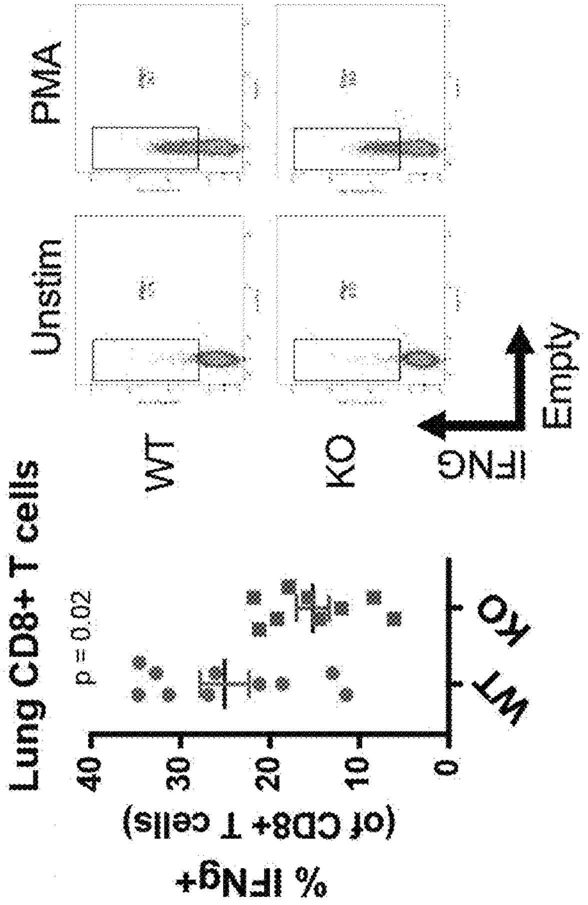
Figure 3D:
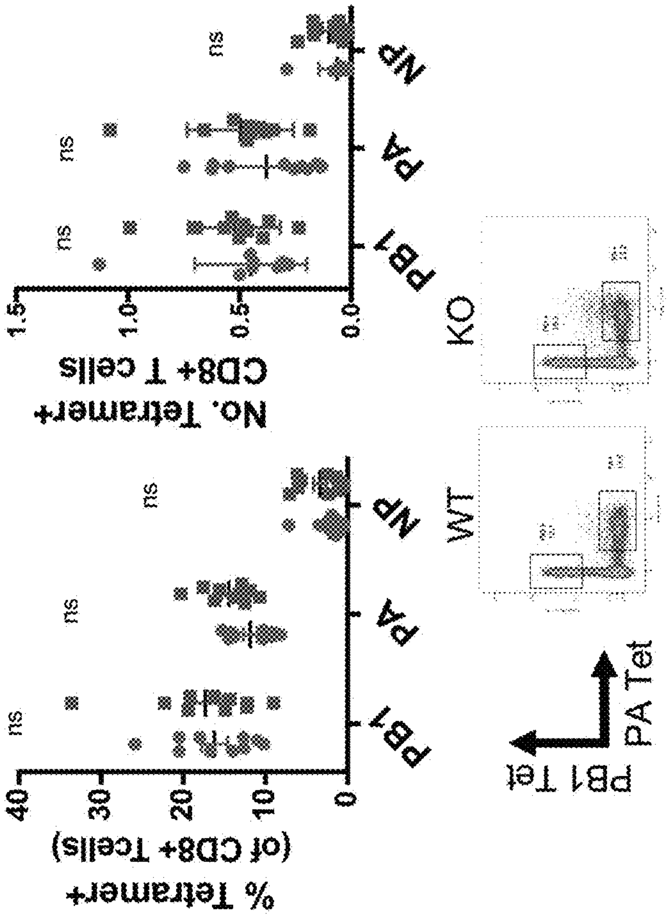

As one of the main drivers of immunopathology in the lung during IAV infection is cytotoxic CD8+ T cells (Duan & Thomas, *Frontiers in Immunology* 7 (2016); La Gruta et al., *Immunology and Cell Biology* 85:85-92 (2007)), we also assessed CD8+ T cell responses in the lungs of ADAMTS-4- and ADAMTS-4+/+ mice at 9 dpi, a time point at which we observe peak T cell responses and widespread lung damage. ADAMTS-4−/− mice had a significantly lower percentage of IFNγ producing CD8+ T cells compared to ADAMTS-4+/+ mice (26.5% vs. 15.7%, p=0.02) in the lung at day 9 (FIG. 3C). However, the percentage of IAV-specific CD8+ T cells, measured using peptide:MHC tetramers for three IAV peptides, did not differ between ADAMTS-4−/− and ADAMTS-4+/+ mice, indicating that ADAMTS-4−/− mice were able to mount IAV-specific T cell responses comparable to wildtype mice (FIG. 3D). In order to determine the abundance and localization of T cells in the lung tissue during infection, we performed immunofluorescence microscopy staining for the T cell marker CD3. Consistent with histology data, we observed in lung sections significantly fewer CD3+ cells in ADAMTS-4−/− compared to ADAMTS-4+/+ mice. In the ADAMTS-4−/− lungs, CD3+ cells were largely absent from areas of high intact versican abundance, a major enzymatic target of ADAMTS-4. In the ADAMTS-4+/+ mice with lower overall abundance of versican, CD3+ cells were dispersed throughout the areas of lung remodeling. Together, these data indicated that, although the quality of the IAV-specific lung CD8 T cell response did not differ between ADAMTS-4$^{-/-}$ and ADAMTS-4+/+ mice, ADAMTS-4+/+ mice had higher frequencies of cytotoxic cells, a pattern likely resulting from a more inflammatory tissue environment characteristic of the ADAMTS-4+/+ lungs.

Figure 3E:
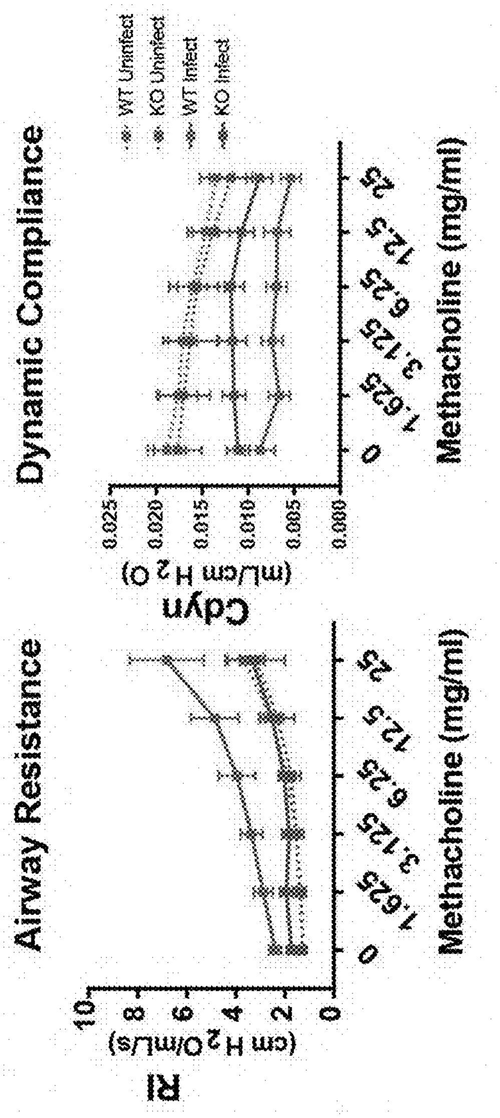

Example 5. Lower Respiratory Tract ADAMTS-4 Levels are Associated with Severe Seasonal and Avian Influenza Infections Finally, we measured the physiological effect of tissue damage resulting from ADAMTS-4 activity on lung function. We assessed airway resistance and dynamic lung compliance in ventilated ADAMTS-4−/− and ADAMTS-4+/+ mice. At 10 dpi, a time point after viral clearance, infected ADAMTS-4−/− mice had lower airway resistance compared to ADAMTS-4+/+ mice at each dose of methacholine, suggesting reduced inflammation in the airways and preservation of lung function (FIG. 3E). Airway resistance in the ADAMTS-4−/− mice was similar to that of uninfected mice. Although compliance was lower than that of uninfected mice, ADAMTS-4−/− mice maintained higher dynamic compliance compared to ADAMTS-4+/+ mice.

To determine if the mechanistic underpinnings of lung immunopathology we defined in mice might be generalizable to humans, we investigated the contribution of ADAMTS-4 and other matrix proteases in the human respiratory tract to the outcome of severe influenza virus infections.

Figure 4A:
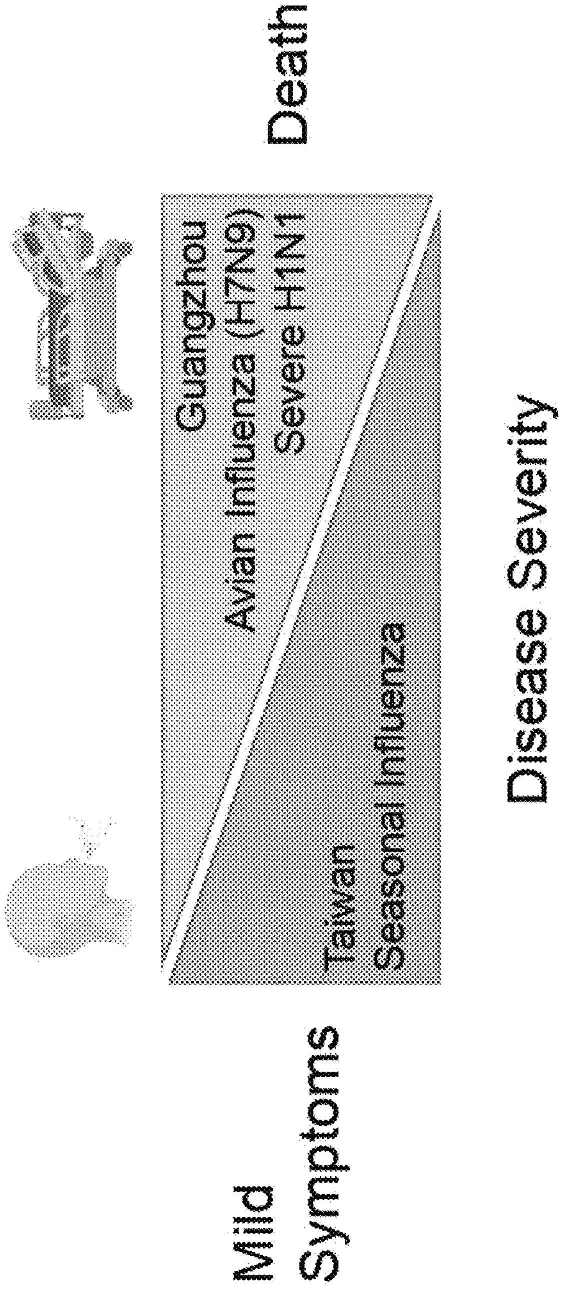

We assessed inflammatory cytokine/chemokine, matrix protease, and TIMP protein levels in two distinct retrospective human cohorts, one from Taipei, Taiwan representing moderate to severe cases of seasonal influenza (37 patients) and the other from Guangzhou, China representing severe cases of H7N9 avian influenza (16 patients) and seasonal H1N1 influenza (14 patients) (FIG. 4A, B). We tested samples from multiple respiratory compartments, including endotracheal aspirates (ETA), sputum, and BAL fluid. While each patient from the Taiwan cohort was sampled at a single time point, the majority of patients from the Guangzhou cohort were sampled at multiple time points following the onset of symptoms.

Figure 4C:
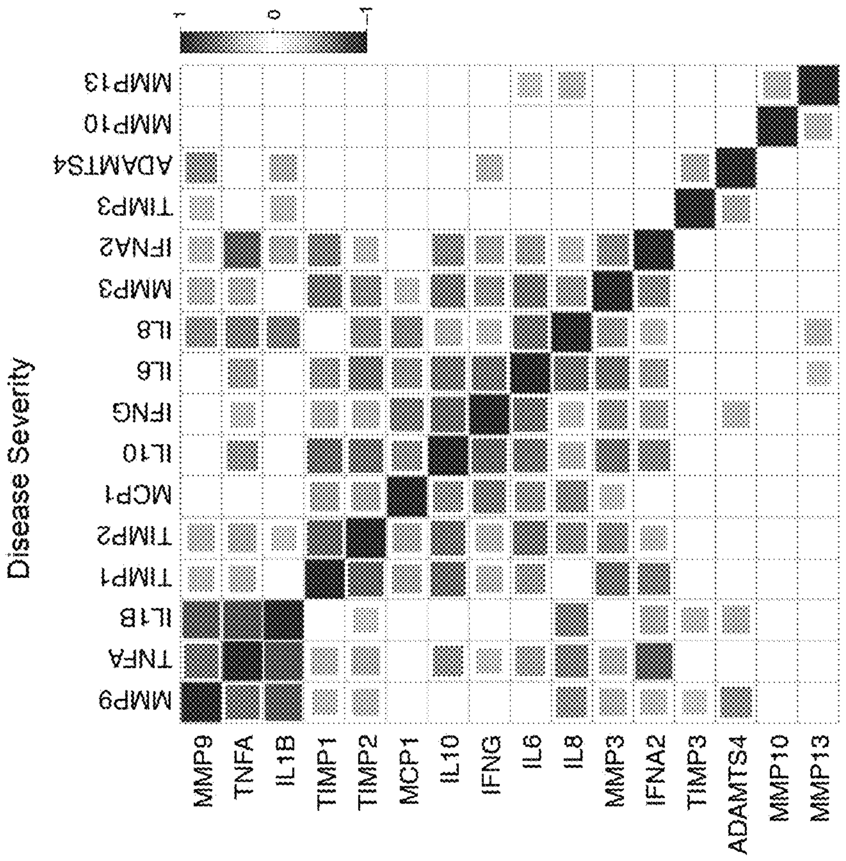
Figure 4D:
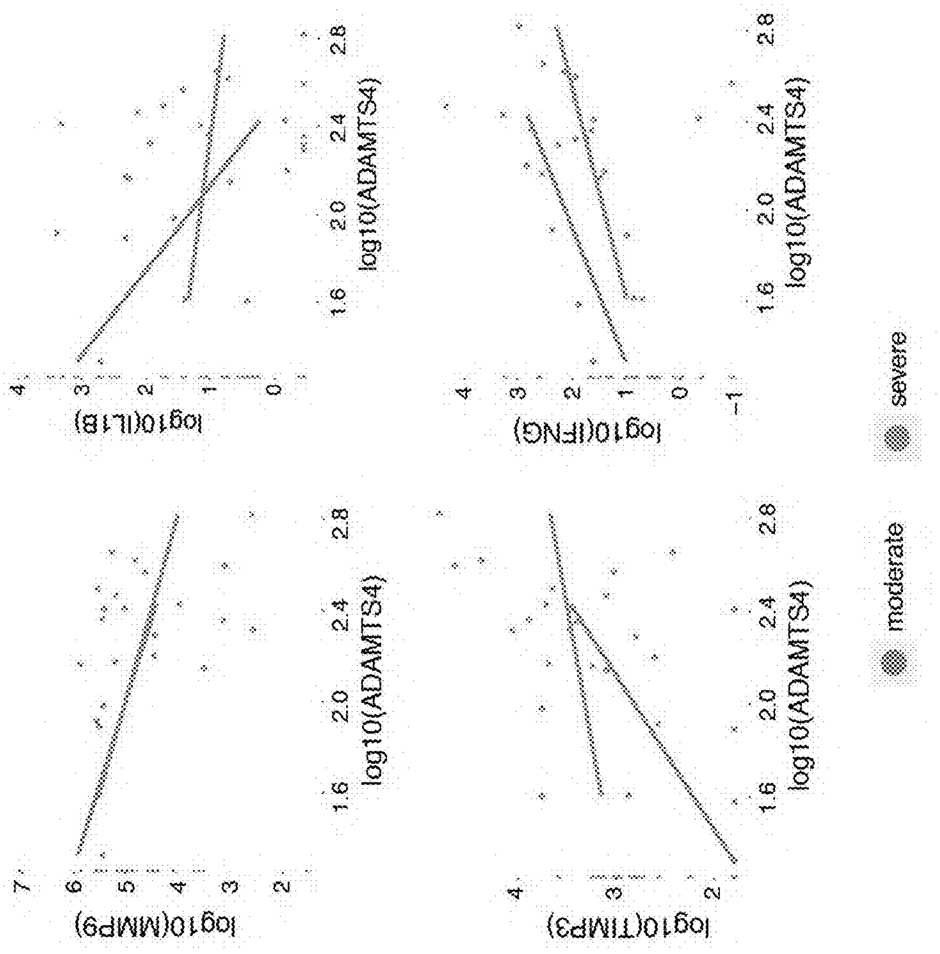

Across both cohorts, we operationally defined groups of patients into two categories: 'moderate' severity disease, those with a hospital stay of less than 20 days and 'severe' disease, those with hospital stay of greater than 20 days. The severe group of patients also included those who died in the hospital following influenza virus infection. In order to identify patterns of regulation among matrix proteases and inflammatory cytokines/chemokines and compare patients with moderate versus severe infections, we generated correlation matrices for a subset of informative analytes using the first available time point for each individual patient, controlling for the potential confounders, including age, sample type, and day of sample collection (FIG. 4C). Hierarchical clustering based on Spearman correlations demonstrated that most of the analytes positively correlated with one another. These analytes included a number of inflammatory cytokines and chemokines (IFNA2, IL-6, IL-8, IL-10, MCP-1) that have previously been shown to be associated with severity of influenza-related disease (Oshansky et al., *Am J Respir Crit Care Med* 189:449-462 (2014); Fiore-Gartland et al., *Front Immunol* 8:1423 (2017)). A subset of these factors (MMP-9, TNFA, and IL-1B), which are all associated with neutrophil responses, were highly correlated with one another. ADAMTS-4 did not, however, group with the majority of these cytokines. Instead, ADAMTS-4 demonstrated significant positive correlations only with IFNG and TIMP-3, an inhibitor of ADAMTS-425,26, and significant negative correlations with MMP-9 and IL-1B (FIG. 4C, D). The directions of these correlations were consistent among moderate and severe cases (FIG. 4D), although the association of ADAMTS-4 and TIMP-3 appeared to be weaker among severe cases. Taken together, these data suggest that ADAMTS-4 is regulated distinctly from other inflammatory mediators and is dissociated from the neutrophil response in the lower respiratory tract, which has previously been implicated in tissue damage during influenza virus infection (Camp & Jonsson, *Front Immunol* 8:550 (2017)).

Figure 4E:
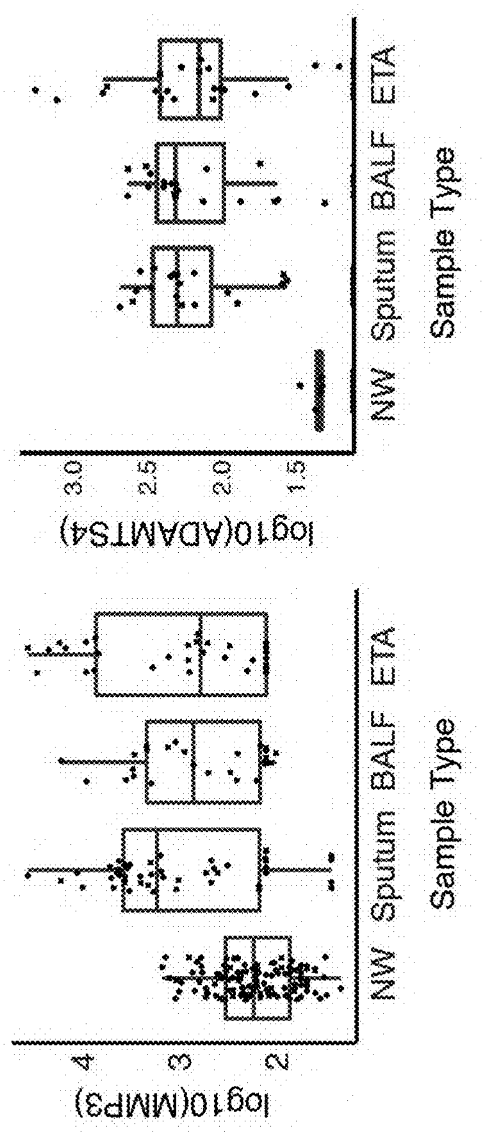

Based on these initial findings, we further explored the association of ADAMTS-4 with severity of influenza disease in the two human cohorts. We first analyzed levels of ADAMTS-4 according to the compartment sampled. For this analysis, we also tested 132 nasal wash samples, representing the upper respiratory tract, from the Taiwan cohort. Although other matrix proteases, including MMP-3, were detectable at high levels in the nasal wash samples from seasonal influenza cases, ADAMTS-4 was detectable at very low levels in 5% (6/131) of samples tested (FIG. 4E). In contrast, ADAMTS-4 was detected at higher frequencies and concentrations in each of the compartments from the lower respiratory tract, including BAL (60%, 15/25), ETA (56%, 19/34) and sputum (35%, 17/48), suggesting that the source of ADAMTS-4 is localized to the lower respiratory tract during infection (although there was no significant difference in ADAMTS-4 levels among distinct sample types from the lower respiratory tract). Concentrations of ADAMTS-4 were significantly lower than other matrix proteases, for example MMP-3 and MMP-9, in lower respiratory tract samples. Low concentrations of ADAMTS-4 in these samples may indicate either a relatively distal site of production within the respiratory tract, or perhaps a pathway more tightly regulated than other matrix proteases, the latter of which would be consistent with observations from in vitro fibroblast stimulation (FIG. 2).

Figure 4F:
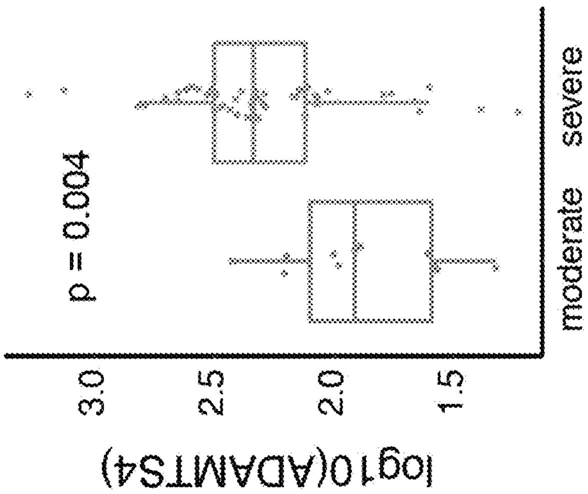

Lastly, we sought to determine whether ADAMTS-4 is a novel lower-respiratory-tract indicator and potential biomarker of disease severity during influenza virus infection. Given the high number of samples with undetectable ADAMTS-4, we only included samples with values above the limit of detection (15 pg/mL). Among all sputum, BALF, and ETA samples, $\log_{10}$ ADAMTS-4 levels were significantly associated with the severity of disease (Chi-square=12.1, p=0.004, adjusted) (FIG. 4F). In addition, $\log_{10}$ ADAMTS-4 levels were significantly negatively associated with days after onset of symptoms (Chi-square=12.0, p=0.004, adjusted). Based on these results, we propose that the levels of ADAMTS-4 protein are an indicator of infection-induced lung damage in the lower respiratory tract and a useful predictor of infection outcome.

Example 6. Treatment of Influenza-Infected Mice with ADAMTS4 1J Inhibitor

The effect of ADAMTS4 inhibitor on the outcome of influenza infection was assessed. To this end, ADAMTS4 Inhibitor 1J was dissolved in 30% (m/v) Sulfobutylether-β-Cyclodextrin. A total of 25 mg/kg of ADAMTS4 inhibitor 1J was administered to each mouse in the treatment group starting at 24 hours prior to infection. The treatment was split into two doses given each day in a volume of 125 μL. The vehicle control group was administered 30% Sulfobutylether-β-Cyclodextrin with the same dosing regimen. Eight-week-old female C57BL/6J mice (from Jackson Laboratories) were anesthetized with 2,2,2-tribromoethanol by intraperitoneal injection and then infected with 2500 50% egg-infectious dose ($EID_{50}$) of influenza virus (A/Puerto Rico/8/1934) intranasally in 30 μL of sterile DPBS. Mice were administered ADAMTS4 inhibitor 1J or the vehicle control through 8 days after the initial inoculation. Mice were monitored for weight loss and signs of morbidity over the course of the infection. Righting reflex was assessed to determine if a mouse required euthanasia. After being placed on their backs, if mice were unable to right themselves after 10 seconds, then the mice were immediately euthanized. For statistical analysis, the treatment and vehicle control survival curves were compared using a Gehan-Breslow-Wilcoxon test. The results are described in FIG. 5.

Figure 5:
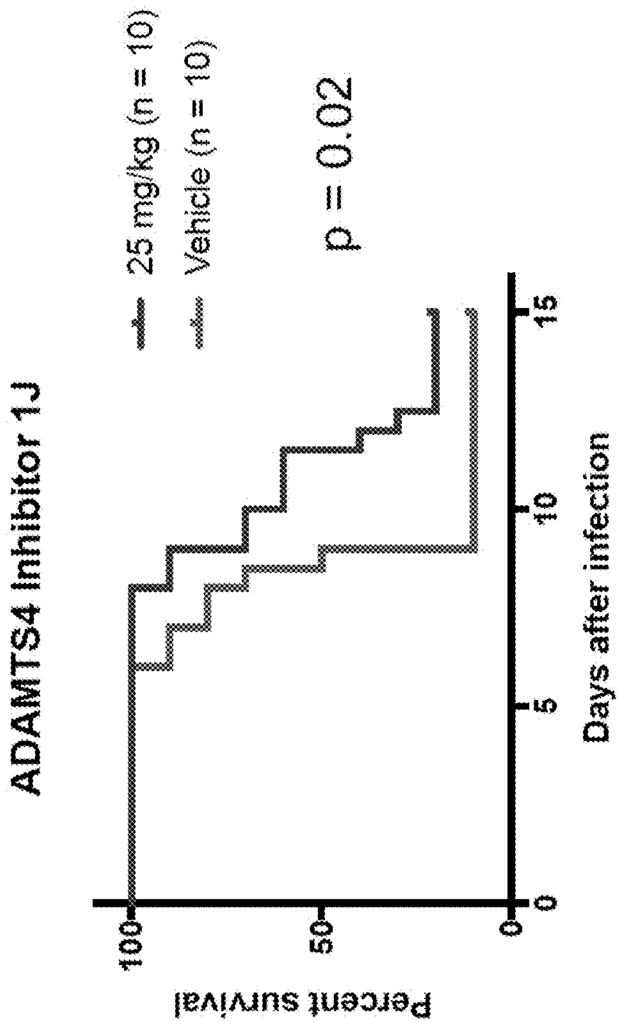
FIG. 5 is a graph showing percent survival in 8-week-old female C57BL/6J mice that were intranasally infected with influenza virus (A/Puerto Rico/8/1934) and were administered either 25 mg/kg ADAMTS4 Inhibitor 1J (n=10) or vehicle control (n=10).

As described in FIG. 5, median survival was significantly improved (p=0.02) in influenza-infected mice that were treated with 25 mg/kg ADAMTS4 1J inhibitor compared to influenza-infected mice that received the vehicle control. Median survival in the ADAMTS4 1J inhibitor-treated group was 11.5 days, as opposed to 8.75 days in the vehicle control group. Together, this result shows the effectiveness of ADAMTS4 inhibitor 1J in promoting survival in influenza-infected mice.

Example 7. Discussion

Surviving a severe respiratory infection is dependent on a careful balance between mounting an immune response which is sufficient to clear the infection and maintaining lung function despite immune-induced tissue damage. During influenza virus infection, viral spread occurs within the epithelial layer on the apical side of the airways. In contrast, inflammatory signals, including cytokines and chemokines, flow from the site of infection to the endothelial layer on the interstitial/basal side to recruit immune cells. By residing at the interface of the epithelial site of infection and the endothelial point of immune-cell entry, fibroblasts are opportunely located to integrate inflammatory signals and coordinate immune responses via modification of the local tissue environment. Lung fibroblasts are well known for their role in promoting fibrosis following lung injury (Wynn, *J Exp Med* 208:1339-1350 (2011)). In the case of severe injury due to respiratory infections, a fibrotic phase, involving the excessive deposition of ECM proteins, occurs at the late stages of lung injury after the resolution of inflammation and may lead to chronic respiratory insufficiency (Thompson et al., *New Engl J Med* 377:562-572 (2017)). Subsets of fibroblasts, such as myofibroblasts, have been recognized as critical drivers of fibrosis in multiple tissues (Wynn, *J Exp Med* 208:1339-1350 (2011)). Recently, several studies have begun to characterize the heterogeneity of fibroblasts and the contribution of distinct subsets of these cells to fibrosis (Shook et al., *Science* 362:eaar2971 (2018); Xie et al., *Cell Rep* 22:3625-3640 (2018)). Here, in Examples 2-5, we provide compelling evidence that lung fibroblasts are also critical for coordinating immune responses at the site of acute infection in the tissue, starting at very early stages of infection and continuing through the repair process. Lung fibroblasts exhibited distinct transcriptional profiles in response to IAV infection, including antiviral and damage-associated responses. During infection, lung fibroblasts respond to IL-1 and TNFA stimulation, transmit inflammatory signals, and modify the extracellular matrix to generate a tissue environment promoting robust immune responses to infection. We propose that the matrix protease activity of the damage-associated fibroblast response represents a promising therapeutic target to produce a tissue tolerant environment that preserves lung function during a severe respiratory infection.

Recently, several studies have described matrix proteases as having both protective (McMahon et al., *PLOS Biol* 14:e1002580 (2016)) and pathogenic (Talmi-Frank et al., *Cell Host Microbe* 20:458-470 (2016); Bradley et al., *PLoS Pathogens* 8:e1002641 (2012); Rojas-Quintero et al., *JCI Insight* 3: e99022 (2018)) roles in the host response to influenza virus infection. These studies have identified the primary sources of these matrix proteases as immune cells (neutrophils, macrophages, T cells). Data presented hereinabove indicate that subsets of inflammatory fibroblasts produce a wide range of matrix proteases in response to cytokine stimulation. The interstitial/basal flow of inflammatory signals and degradation of the lung ECM mediated by fibroblasts likely contribute to the lethal immunopathology that can result from severe IAV infection. All subsets of lung fibroblasts had very low rates of infection compared to epithelial cells indicating that they are not likely to play a role in viral sensing. Instead, fibroblasts integrate danger signals from epithelial cells and resident immune cells to produce a spectrum of inflammatory cytokines and matrix proteases to modify the local tissue environment and help coordinate early host responses. Based on scGEX profiling of lung cells from in vivo infections and of in vitro stimulations, we demonstrate that lung fibroblasts are capable of producing a wide range of inflammatory cytokines and matrix proteases in response to IL-1 and TNFA stimulation. The similar ECM-related transcriptional profiles induced by IL-1 cytokines and TNFA suggests that NFkB plays an important role in mediating these responses in fibroblasts. IL-1A derived from damaged epithelial cells has previously been identified as a major driver of cytokine and chemokine production in lung fibroblasts (Suwara et al., *Mucosal Immunol* 7:684-693 (2014)). The upregulation of ADAMTS-4 in response to IL-1 and TNFA is consistent with previous reports using synovial fibroblasts, critical drivers of inflammation in osteoarthritis (Corps et al., *Matrix Biol* 27:393-401 (2008); Potter-Perigo et al., *Am J Respir Cell Mol Biol* 43:109-120 (2010)). Many matrix proteases belonging to the MMP and ADAMTS gene families have overlapping enzymatic activity based on their ability to degrade substrates in vitro (Bonnans & Werb, *Nat Rev Mol Cell Biol* 15:786-801 (2014)), and several ADAMTS enzymes have versicanase activity (Kelwick et al., *Genome Biology* 16, (2015); Apte, *J Biol Chem* 284:31493-31497 (2009)). Despite this potential redundancy, mice deficient for ADAMTS-4 exhibited an increased abundance of intact versican with a corresponding reduction in immune cell infiltration compared to ADAMTS-4 sufficient animals, suggesting that there is little or no compensatory expression of other versicanases in vivo.

The role of IL-1 cytokines in responding to IAV infection has been extensively studied (Iwasaki & Pillai, *Immunology* 14:315-328 (2014)), and IL-1B, resulting from NLRP3 inflammasome activation (Allen et al., *Immunity* 30:556-565 (2009); Ichinohe et al., *Nat Immunol* 11:404-410 (2010)) has been implicated in many aspects of the host response to infection, from generating effective IAV-specific cytotoxic T cell responses (Pang et al., *Nat Immunol* 14:246-253 (2013)) to playing a role in healing responses (Thomas et al., *Immunity* 30:566-575 (2009)). The induction of ECM-related gene expression, including genes encoding both ECM structural proteins and remodeling enzymes, in fibroblasts by IL-1 cytokines provides a novel mechanism by which IL-1 contributes to lung tissue remodeling in response to respiratory infection. IL-1 cytokines can have pleiotropic effects on infection outcomes depending on the magnitude and timing of expression. Data from both mouse models and human cases of severe IAV infections suggest that prolonged IL-1B expression in the lower respiratory tract prevent recovery from infection (Tate et al., *Sci Rep* 6, 27912 (2016); Wang et al., *Proc Natl Acad Sci* 111:769-774 (2014); Yang et al., *PLOS ONE* 10: e0117846 (2015)). There is also evidence for caspase-independent cleavage and activation of pro-IL1B by MMP-9, MMP-3, and MMP-2 (Schönbeck et al., *J Immunol* 161:3340-3346 (1998)), the latter being a matrix protease that was expressed in the majority of fibroblast subsets identified here by scGEX. Even within fibroblasts, IL-1 stimulation in vitro upregulated gene expression of a wide variety of effectors, including matrix proteases, inhibitors of matrix proteases, ECM structural proteins, growth factors, and inflammatory cytokines associated with both IRFib and DRFib signatures. Damage-associated signals, such as IL-1A, can promote the expression of genes typically induced by type-I interferon signaling in fibroblasts (Orzalli et al., *Mol Cell* 71:825-840.e6 (2018)), possibly implicating IL-1 cytokines in broad regulation of fibroblast responses to infection in cases of viral antagonism of the interferon response. Direct inhibition of IL-1 cytokines likely would not be an effective way to limit tissue damage. Instead, inhibiting specific effectors downstream of IL-1 signaling in fibroblasts, such as ADAMTS-4, represents a more targeted approach to preserving lung function and improving outcomes following severe respiratory infections. Our data demonstrate that despite a reduced quantitative magnitude of inflammatory T cell response in ADAMTS-4−/− mice, the quality of the IAV-specific response was unaffected (FIGS. 3C, 3D). Thus, targeting these down-stream remodeling enzymes to preserve lung integrity may preserve immunological memory protective against future IAV challenge.

Our data from the mouse model suggest that deficiency of ADAMTS-4 activity in the lung preserves intact ECM-localized versican and modulates immune cell migration into the areas of infection, in particular CD8+ T cells. Previous studies have indicated an immunomodulatory role of intact versican in various disease models (McMahon et al., *PLOS Biol* 14, e1002580 (2016); Chang et al., *Am J Physiol Lung Cell Mol Physiol* 313:L1069-L1086 (2017); Hope et al., *Blood* 128:680-685 (2016); Hope et al., *J Immunol* 199:1933-1941 (2017)). Here, we propose a mechanism by which specialized populations of infection-induced fibroblasts act a network to shape the local lung tissue environment. IRFibs produce VCAN in response to infection while DRFibs produce ADAMTS-4 to modify its immunomodulatory state. This division of labor among fibroblasts represents an opportunity to modulate distinct functions or specific effector molecules of these cells to influence the trajectory of the host response.

Our data from two human cohorts of influenza infection indicate that ADAMTS-4 could be a useful biomarker of severe disease and a potential therapeutic target for limiting excessive immunopathology in severe infections. ADAMTS-4 protein was detectable in lower respiratory tract samples that require direct lower respiratory tract sampling (ETA, BAL) and in those that do not (sputum). Relatively low concentrations in the lower respiratory tract compared to other matrix proteases may bode well for ADAMTS-4 as a therapeutic target because there could be a low threshold of ADAMTS-4 inhibition to limit the effect of its activity. Subsequent studies will be needed to validate the predictive ability of ADAMTS-4 for severe influenza virus infection in other cohorts due to the relatively small sample size in each of our cohorts. Further, underlying differences in the patient populations for which we were unable to control, due to sample size as well as timing of sampling, are limitations of this study. The grouping of patients into moderate and severe cases based on length of hospital stay and outcome (discharge or death) was designed to maintain comparable numbers in each group and to limit multiple testing. The role of ADAMTS-4 in promoting excessive immunopathology and contributing to lung damage also warrants further investigation in other models of severe respiratory infection.

Currently, there are no effective therapeutics for treating severe complications of IAV infections, such as ARDS, and treatment for severe disease is supportive, including supplemental oxygen and mechanical ventilation (Thompson et al., *New Engl J Med* 377:562-572 (2017)). For severe influenza virus infections, antivirals have a short therapeutic window, approximately 48-72 hours, within which very few patients present for treatment (Govorkova & McCullers, Therapeutics Against Influenza. in Swine Influenza (eds. Richt, J. A. & Webby, R. J.) 370, 273-300 (Springer Berlin Heidelberg, 2011)). As our data establish that fibroblasts are a critical tissue-organizing cell type during acute respiratory infection, we propose that targeting the matrix protease activity of tissue-damage responsive fibroblasts could provide clinical benefits, both by limiting excessive inflammation and sparing the integrity of lung tissue, which together could help preserve normal lung function. These qualities suggest that ADAMTS-4 activity would be an ideal target for therapeutic intervention in severe lower respiratory tract infection and ARDS.

The contents of all references, patents, pending patent applications, and publications cited throughout this application are hereby expressly incorporated by reference herein in their entirety.

Those skilled in the art will recognize, or be able to ascertain using no more than routine experimentation, many equivalents to the specific embodiments of the invention described herein. Such equivalents are intended to be encompassed by the following claims.

What is claimed is:

1. A pharmaceutical composition comprising:

(i) a therapeutically effective amount of at least one ADAMTS4 inhibitor, wherein the ADAMTS4 inhibitor is:

(a) a compound represented by formula (I)

(I)

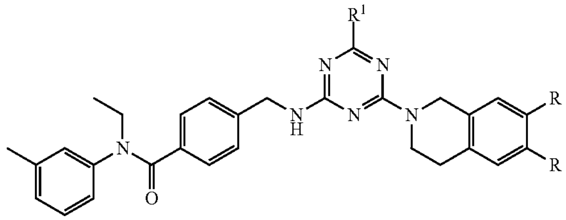

wherein R is Ome; and

R1 is

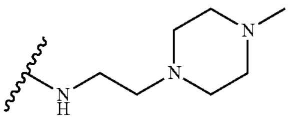 [SMILES: *NCCN1CCN(C)CC1]

or a pharmaceutically acceptable salt thereof, or (b) a compound represented by formula (II)

(II)

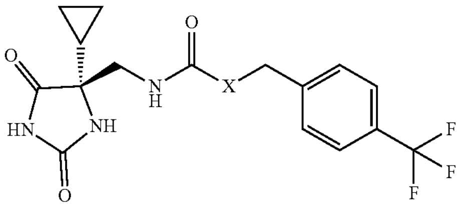

wherein X is

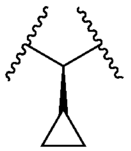

or a pharmaceutically acceptable salt thereof;

and (ii) a therapeutically effective amount of at least one antibiotic.

2. The pharmaceutical composition of claim 1, wherein the ADAMTS4 inhibitor is 4-(((4-(6,7-dimethoxy-3,4-dihydroisoquinolin-2(1H)-yl)-6-(((4-methylpiperazin-1-yl)methyl)amino)-1,3,5-triazin-2-yl)amino)methyl)-N-ethyl-N-(m-tolyl)benzamide, or a pharmaceutically acceptable salt thereof.

3. The pharmaceutical composition of claim 1, wherein the ADAMTS4 inhibitor is (S)-2-Cyclopropyl-N—(((R)-4-cyclopropyl-2,5-dioxoimidazolidin-4-yl)methyl)-3-(4-(trifluoromethyl)phenyl)-propanamide.

4. The pharmaceutical composition of claim 1, wherein the antibiotic is a broad spectrum antibiotic.

5. The pharmaceutical composition of claim 1, further comprising a pharmaceutically acceptable carrier.

6. The pharmaceutical composition of claim 1, further comprising one or more antiviral therapeutic.

7. The pharmaceutical composition of claim 6, wherein the antiviral therapeutic is effective against influenza virus.

8. A method for treating influenza A infection in a subject in need thereof, the method comprising administering to the subject:

(i) a therapeutically effective amount of at least one ADAMTS4 inhibitor, wherein the ADAMTS4 inhibitor is:

(a) a compound represented by formula (I)

(I)

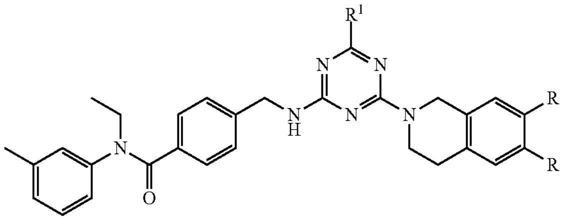

wherein R is Ome; and

R1 is

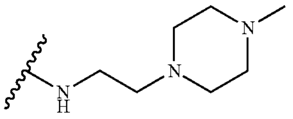 [SMILES: *NCCN1CCN(C)CC1]

or a pharmaceutically acceptable salt thereof, or (b) a compound represented by formula (II)

(II)

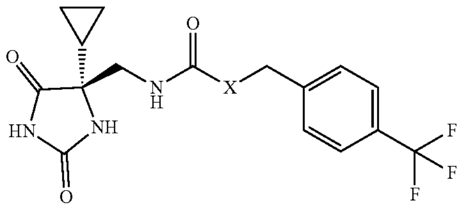

wherein X is

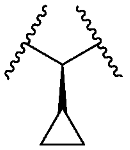

or a pharmaceutically acceptable salt thereof;

and (ii) a therapeutically effective amount of at least one antibiotic.

9. The method of claim 8, wherein treating the infection comprises reducing at least one symptom of the infection, wherein the at least one symptom is a symptom of a secondary bacterial infection developed following a viral infection.

10. The method of claim 8, wherein the method comprises administering:

the antibiotic prior to administering the ADAMTS4 inhibitor;

the antibiotic subsequent to administering the ADAMTS4 inhibitor; or the antibiotic and the ADAMTS4 inhibitor concomitantly.

11. The method of claim 8, further comprising administering one or more antiviral therapeutic.

12. The method of claim 8, wherein the method reduces inflammation, immune cell infiltration, and/or tissue damage associated with the infection.

13. The method of claim 12, wherein the method reduces mRNA and/or protein expression of one or more inflammatory cytokines or chemokines.

14. The method of claim 13, wherein the method reduces mRNA and/or protein expression of TNFA and MCP-1.

15. The method of claim 8, wherein the infection is a respiratory infection.

* * * * *